(12) United States Patent
Jackson et al.

(10) Patent No.: US 12,329,549 B2
(45) Date of Patent: Jun. 17, 2025

(54) ENDOSCOPE STORAGE TRAY HAVING APERTURES AND METHOD OF USE

(71) Applicant: Medivators Inc., Minneapolis, MN (US)

(72) Inventors: Mark Jackson, Great Wakering (GB); Gary Spencer, Rayleigh (GB); Colin Oxford, Canvey Island (GB); Stephen Nichols, Witham (GB)

(73) Assignee: Medivators Inc., Minneapolis, MN (US)

( * ) Notice: Subject to any disclaimer, the term of this patent is extended or adjusted under 35 U.S.C. 154(b) by 361 days.

(21) Appl. No.: 17/618,989

(22) PCT Filed: Jun. 8, 2020

(86) PCT No.: PCT/US2020/036635
§ 371 (c)(1),
(2) Date: Dec. 14, 2021

(87) PCT Pub. No.: WO2020/256990
PCT Pub. Date: Dec. 24, 2020

(65) Prior Publication Data
US 2022/0304762 A1     Sep. 29, 2022

Related U.S. Application Data

(60) Provisional application No. 62/864,076, filed on Jun. 20, 2019.

(51) Int. Cl.
*A61L 2/26* (2006.01)
*A61B 50/22* (2016.01)
(Continued)

(52) U.S. Cl.
CPC .......... *A61B 50/33* (2016.02); *A61B 1/00144* (2013.01); *A61B 2050/006* (2016.02)

(58) Field of Classification Search
CPC ... A61B 50/33; A61B 50/34; A61B 2050/006; A61B 1/00144; A61B 1/00147;
(Continued)

(56) References Cited

U.S. PATENT DOCUMENTS

| 803,102 A | 10/1905 | Harris |
|---|---|---|
| 1,592,726 A | 7/1926 | Dunbar |

(Continued)

FOREIGN PATENT DOCUMENTS

| AU | 2018211256 A1 | 2/2019 |
|---|---|---|
| CN | 108030556 A | 5/2018 |

(Continued)

OTHER PUBLICATIONS

ARES flexible endoscope automated reprocessing system' (Steelco) Jul. 12, 2018 (Jul. 12, 2018) [retreived from the internet on Aug. 24, 2020 (Aug. 24, 2020) at https://web.archive.org/web/20180712214831/http://www.peacocks.net/_filecache/9e4/a6e/550-steelco-ares-rev04.pdf].

(Continued)

*Primary Examiner* — Gideon R Weinerth

(57) ABSTRACT

An endoscope tray is provided. The tray comprises an interior for storage of an endoscope. The interior has an upstanding element having a top surface, and a plurality of apertures disposed on at least a portion of the top surface of the upstanding element to facilitate drainage of fluids. Systems and methods are also provided.

19 Claims, 26 Drawing Sheets

(51) Int. Cl.
*A61B 50/33* (2016.01)
*B65D 1/34* (2006.01)
*B65D 81/26* (2006.01)
*A61B 1/00* (2006.01)
*A61B 50/00* (2016.01)

(58) Field of Classification Search
CPC ........ A61B 2050/005; A61B 2050/314; A61L 2/26; A61L 2/07; A61L 2202/24; A61L 2202/18; A61L 2202/182; B08B 3/045; B08B 3/047; B65D 1/34; B65D 1/36
USPC .............................. 134/22.1, 166 R; 206/364
See application file for complete search history.

(56) References Cited

U.S. PATENT DOCUMENTS

| | | | |
|---|---|---|---|
| 1,717,974 A | 6/1929 | Heinrichs | |
| 2,080,108 A | 5/1937 | Bradstein | |
| 2,214,946 A | 9/1940 | Werner | |
| 2,412,325 A | 12/1946 | Devine et al. | |
| 3,157,902 A | 11/1964 | Hardwick | |
| 3,757,990 A | 9/1973 | Buth | |
| 3,770,119 A | 11/1973 | Hultberg et al. | |
| 3,949,934 A | 4/1976 | Goglio | |
| 4,042,109 A | 8/1977 | Barcan | |
| 4,053,280 A | 10/1977 | Salisbury | |
| 4,256,225 A | 3/1981 | Jackson | |
| 4,466,552 A | 8/1984 | Butterworth et al. | |
| 4,574,978 A | 3/1986 | Hodges | |
| 4,583,643 A | 4/1986 | Sanderson | |
| 4,704,254 A | 11/1987 | Nichols | |
| 4,730,729 A | 3/1988 | Harry | |
| 4,750,619 A | 6/1988 | Cohen et al. | |
| 4,754,595 A * | 7/1988 | Sanderson ......... B65D 81/2023 53/425 | |
| 4,903,718 A | 2/1990 | Sullivan | |
| 4,948,266 A | 8/1990 | Bencic | |
| 5,108,195 A | 4/1992 | Perron | |
| 5,207,325 A | 5/1993 | Kennedy | |
| 5,263,777 A | 11/1993 | Domke | |
| 5,288,467 A | 2/1994 | Biermaier | |
| 5,295,606 A | 3/1994 | Karwoski | |
| 5,392,917 A | 2/1995 | Alpern et al. | |
| 5,409,126 A | 4/1995 | Demars | |
| 5,443,801 A | 8/1995 | Langford | |
| 5,733,243 A | 3/1998 | Yabe et al. | |
| 5,882,589 A | 3/1999 | Mariotti | |
| 5,989,608 A | 11/1999 | Mizuno | |
| 6,029,844 A | 2/2000 | Brady | |
| 6,041,794 A | 3/2000 | Lin et al. | |
| 6,139,185 A | 10/2000 | Hamilton et al. | |
| 6,151,910 A | 11/2000 | Hazen | |
| 6,210,638 B1 | 4/2001 | Grieco et al. | |
| 6,235,692 B1 | 5/2001 | Scoville et al. | |
| 6,305,567 B1 | 10/2001 | Sulpizio | |
| 6,312,645 B1 | 11/2001 | Lin et al. | |
| 6,378,721 B1 | 4/2002 | Williams | |
| 6,380,524 B1 | 4/2002 | Keller | |
| 6,622,862 B1 | 9/2003 | Corrado | |
| 6,622,864 B1 | 9/2003 | Debbs et al. | |
| 6,641,781 B2 * | 11/2003 | Walta ................ A61B 50/10 134/92 | |
| 6,733,803 B1 | 5/2004 | Karsten | |
| 6,749,063 B2 * | 6/2004 | Parker ................ A61B 50/30 206/363 | |
| 6,916,456 B2 | 7/2005 | Martineau et al. | |
| 6,994,823 B2 | 2/2006 | Hight, III | |
| 7,041,941 B2 | 5/2006 | Faries, Jr. et al. | |
| D531,734 S * | 11/2006 | Haunschild ................ D24/217 | |
| 7,132,089 B2 | 11/2006 | Lacabanne | |
| 7,178,555 B2 | 2/2007 | Engel et al. | |
| 7,476,368 B2 | 1/2009 | Sargent et al. | |
| 7,630,791 B2 | 12/2009 | Nguyen et al. | |
| 7,993,602 B2 | 8/2011 | Moriyama et al. | |
| 8,287,816 B2 | 10/2012 | Kral | |
| 8,414,471 B2 | 4/2013 | Mandava et al. | |
| 8,435,445 B2 | 5/2013 | Kral | |
| 8,454,901 B1 | 6/2013 | Snyder, III | |
| 8,733,551 B2 * | 5/2014 | Parker ................ A61B 1/00144 206/570 | |
| 8,795,603 B2 | 8/2014 | Ghelman et al. | |
| 8,851,287 B2 | 10/2014 | Becklin | |
| 8,905,258 B2 | 12/2014 | Javid et al. | |
| 9,348,013 B2 | 5/2016 | Rahim et al. | |
| 9,703,264 B2 | 7/2017 | Freijsen et al. | |
| 9,910,965 B2 | 3/2018 | Bufalini et al. | |
| D818,841 S | 5/2018 | Newton | |
| D819,409 S | 6/2018 | Newton | |
| 10,405,938 B2 | 9/2019 | Ramsey | |
| 10,418,831 B2 | 9/2019 | Racenet et al. | |
| 10,456,494 B2 * | 10/2019 | Roudebush ............... A61L 2/26 | |
| 10,463,441 B2 | 11/2019 | Tate et al. | |
| D909,883 S | 2/2021 | Newton | |
| D921,490 S | 6/2021 | Newton | |
| 11,445,900 B2 | 9/2022 | King et al. | |
| 11,696,811 B2 * | 7/2023 | Dalena ................ A61B 50/33 206/363 | |
| 2003/0078472 A1 | 4/2003 | Parker | |
| 2004/0101456 A1 | 5/2004 | Kuroshima et al. | |
| 2005/0260097 A1 | 11/2005 | Williams et al. | |
| 2006/0193761 A1 | 8/2006 | Moriyama et al. | |
| 2007/0215507 A1 | 9/2007 | Glenn et al. | |
| 2007/0228080 A1 | 10/2007 | Lin et al. | |
| 2008/0251102 A1 | 10/2008 | Haack et al. | |
| 2009/0091453 A1 | 4/2009 | Ishida et al. | |
| 2009/0104094 A1 | 4/2009 | Affaitati et al. | |
| 2009/0123333 A1 | 5/2009 | Parker et al. | |
| 2009/0206674 A1 | 8/2009 | Noguchi et al. | |
| 2009/0261549 A1 * | 10/2009 | Kral ....................... A61B 50/10 280/47.35 | |
| 2010/0176016 A1 * | 7/2010 | Pell ....................... A61B 50/33 206/370 | |
| 2010/0189598 A1 * | 7/2010 | Fraundorfer ............ A61L 2/186 422/292 | |
| 2011/0002811 A1 * | 1/2011 | Dane ...................... A61B 50/30 422/243 | |
| 2011/0192744 A1 * | 8/2011 | Parker ................... A61B 50/30 206/363 | |
| 2012/0152289 A1 * | 6/2012 | Smith ....................... A61L 2/26 134/109 | |
| 2013/0019910 A1 * | 1/2013 | Ledel ...................... B08B 3/047 134/166 C | |
| 2013/0105344 A1 * | 5/2013 | Hartley ............... A61B 1/00144 206/363 | |
| 2013/0192647 A1 * | 8/2013 | Ledel ....................... A61L 2/24 134/166 R | |
| 2014/0069841 A1 * | 3/2014 | Pizzato ................... B25H 3/026 206/570 | |
| 2014/0083886 A1 * | 3/2014 | Winterrowd ........... A61B 50/30 206/370 | |
| 2014/0182629 A1 * | 7/2014 | Dromard ................ B08B 9/023 134/170 | |
| 2014/0270583 A1 | 9/2014 | Anderson | |
| 2014/0339114 A1 * | 11/2014 | Griffin ................... A61B 50/20 206/370 | |
| 2014/0353203 A1 | 12/2014 | Hu et al. | |
| 2015/0257632 A1 | 9/2015 | Ramsey | |
| 2015/0259122 A1 * | 9/2015 | Parker ................... B65B 31/04 53/410 | |
| 2015/0272680 A1 | 10/2015 | Suzuki | |
| 2016/0058900 A1 * | 3/2016 | Sato ...................... A61B 1/123 134/56 R | |
| 2016/0081540 A1 | 3/2016 | Suzuki | |
| 2016/0095508 A1 | 4/2016 | Terliuc et al. | |
| 2016/0249915 A1 | 9/2016 | Beckman et al. | |
| 2017/0056122 A1 * | 3/2017 | Ramsey ................ A61B 50/36 | |
| 2017/0091389 A1 | 3/2017 | Dukatz | |
| 2017/0172397 A1 | 6/2017 | Zardini | |
| 2018/0028703 A1 | 2/2018 | Mclaughlin et al. | |
| 2018/0071045 A1 * | 3/2018 | Cohen .................... A61B 50/30 | |
| 2018/0134453 A1 | 5/2018 | Wassenburg | |
| 2019/0021806 A1 | 1/2019 | Turbett | |

(56) References Cited

U.S. PATENT DOCUMENTS

| | | | |
|---|---|---|---|
| 2019/0365500 A1* | 12/2019 | Erdmann | B08B 9/0328 |
| 2020/0118674 A1 | 4/2020 | Le et al. | |
| 2020/0187767 A1* | 6/2020 | Kramer | A61B 1/121 |
| 2020/0205925 A1* | 7/2020 | Cummings | B65D 25/16 |
| 2020/0315731 A1* | 10/2020 | Zardini | A61B 50/34 |
| 2021/0076923 A1* | 3/2021 | Awau | A61B 1/00011 |
| 2021/0128768 A1* | 5/2021 | Jackson | A61B 50/20 |
| 2021/0138517 A1* | 5/2021 | Kakar | B08B 9/023 |
| 2021/0186640 A1* | 6/2021 | Dalena | A61B 50/13 |
| 2021/0186641 A1* | 6/2021 | Cummings | A61B 50/33 |
| 2021/0187141 A1* | 6/2021 | Crotti | A61L 2/26 |
| 2021/0212796 A1 | 7/2021 | Crotti | |
| 2021/0356051 A1 | 11/2021 | Gray-Dreizler et al. | |
| 2021/0401528 A1* | 12/2021 | Wilson | A61B 46/10 |
| 2022/0211458 A1 | 7/2022 | Jackson et al. | |
| 2022/0304560 A1* | 9/2022 | Jackson | A61B 50/13 |
| 2022/0304762 A1* | 9/2022 | Jackson | A61B 1/00144 |
| 2022/0304764 A1* | 9/2022 | Jackson | A61L 2/26 |
| 2022/0387651 A1* | 12/2022 | Kendrick | A61L 2/22 |
| 2022/0392102 A1* | 12/2022 | Ohara | A61B 1/00059 |
| 2023/0082582 A1* | 3/2023 | Jackson | A61B 50/33 |
| | | | 206/363 |
| 2023/0285614 A1* | 9/2023 | Kotani | A61B 50/33 |

FOREIGN PATENT DOCUMENTS

| | | |
|---|---|---|
| DE | 202016105248 | 12/2016 |
| EP | 0091792 81 | 1/1988 |
| EP | 0830295 A1 | 3/1998 |
| EP | 2689706 A2 | 1/2014 |
| EP | 2900117 A1 | 8/2015 |
| JP | 2007054343 | 3/2007 |
| JP | 2009172228 | 8/2009 |
| JP | 2008054861 | 3/2020 |
| WO | 9607364 | 3/1996 |
| WO | 2011151641 | 12/2011 |
| WO | 2018024690 | 2/2018 |
| WO | 2018152400 A1 | 8/2018 |

OTHER PUBLICATIONS

International Preliminary Report on Patentability dated Dec. 30, 2021, of International PCT Application No. PCT/US/2020/036618 dated Jun. 8, 2020.

International Search Report and Written Opinion of the International Searching Authority Dated Sep. 9, 2020, of International PCT Application No. PCT/US2020/036618 filed Jun. 8, 2020.

Steelco ED200 Endoscope Drying/Storage Cabinet' (Peacocks Medical Group) Jun. 20, 2018(Jun. 28, 2018) [retreived from the internet on Aug. 24, 2020 (Aug. 24, 2020) at https://web.archive.org/web/20180620034054/https://www.peacocks.net/medical-decontamination/endoscopy/endoscopy-drying-cabinetslsteelco-ed200.

International Preliminary Report on Patentability dated Dec. 30, 2021, of International PCT Application No. PCT/US/2020/036630 dated Jun. 8, 2020.

International Preliminary Report on Patentability dated Dec. 30, 2021, of International PCT Application No. PCT/US/2020/036635 dated Jun. 8, 2020.

International Preliminary Report on Patentability dated Sep. 9, 2022 of International PCT Application No. PCT/US/2021/018463 dated Feb. 18, 2021.

International Preliminary Report on Patentability dated Sep. 30, 2021, of International PCT Application No. PCT/US2020/019640, dated Feb. 25, 2020.

International Search Report and Written Opinion mailed May 6, 2021, in International Application No. PCT/US2021/018463 filed Feb. 18, 2021.

International Search Report and Written Opinion mailed Nov. 20, 2020, in International Application No. PCT/US2020/036635 filed Jun. 8, 2020.

International Search Report and Written Opinion of the International Searching Authority Dated Jun. 5, 2020, of International PCT Application No. PCT/US2020/019640 filed Feb. 25, 2020.

International Search Report and Written Opinion of the International Searching Authority Dated Sep. 3, 2020, of International PCT Application No. PCT/US2020/036630 filed Jun. 8, 2020.

* cited by examiner

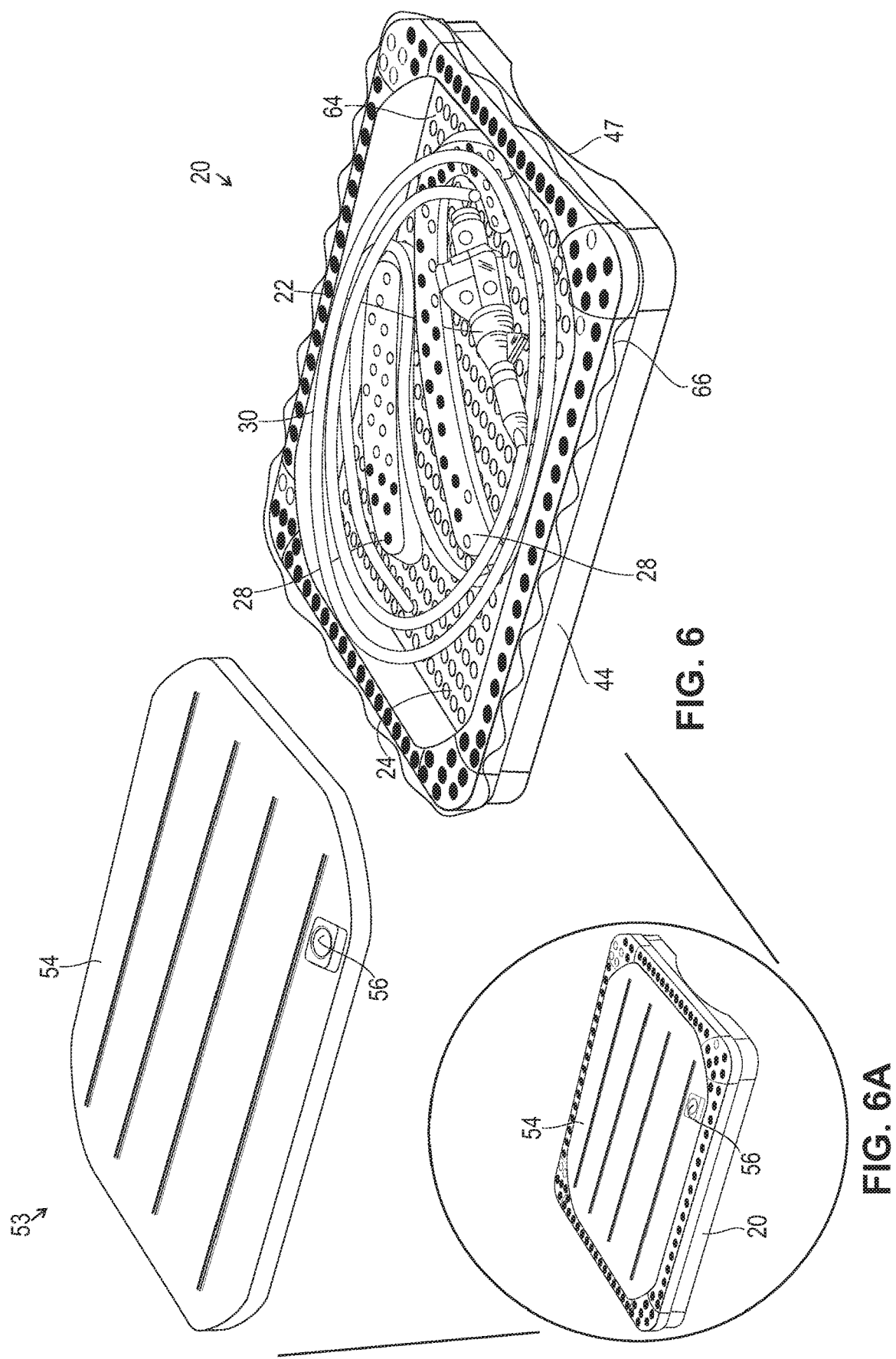

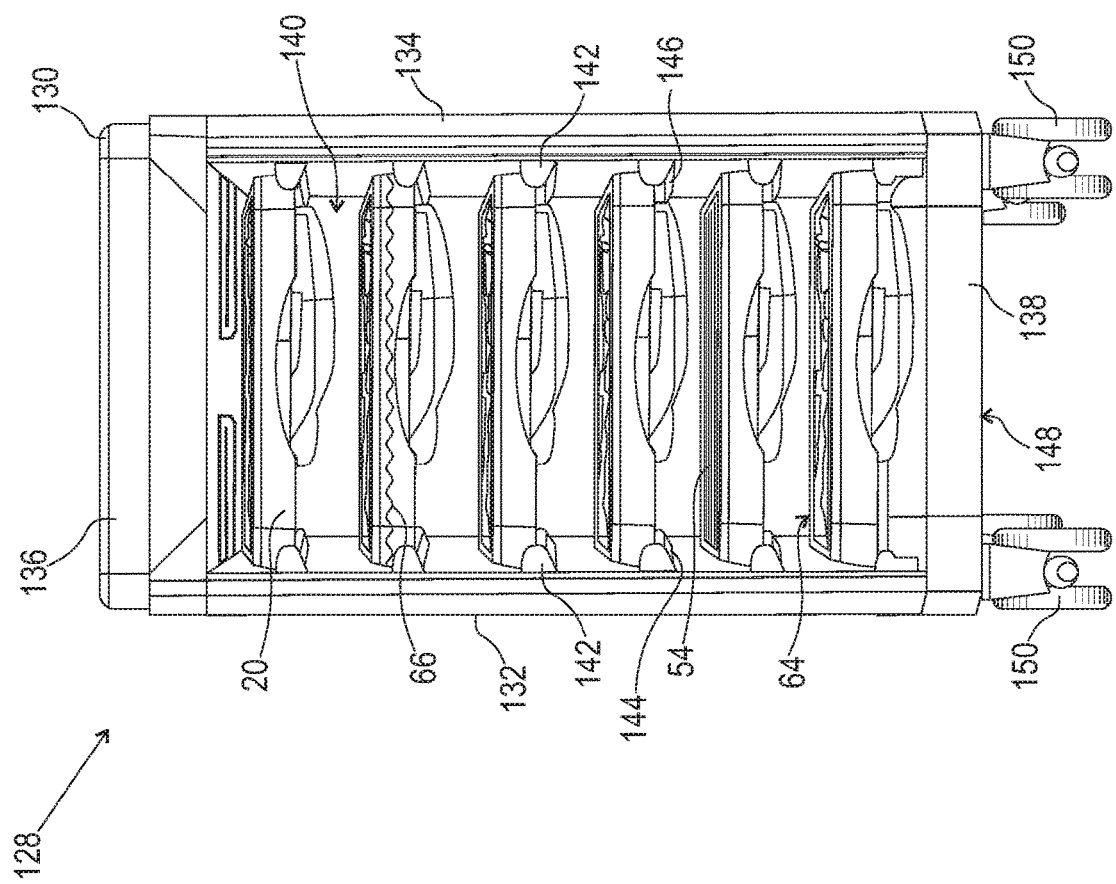

ENDOSCOPE STORAGE TRAY HAVING APERTURES AND METHOD OF USE

PRIORITY CLAIM

This application claims priority to and the benefit of U.S. Provisional application with Ser. No. 62/864,076, filed on Jun. 20, 2019, entitled ENDOSCOPE STORAGE TRAY HAVING APERTURES AND METHOD OF USE, which is herein incorporated by reference in its entirety.

BACKGROUND

Endoscopes are well-known in the art and are commonly used for numerous medical procedures. After each use, an endoscope will undergo reprocessing by cleaning, disinfection and/or sterilization to reduce or prevent contaminants from settling onto the endoscope, as well as to prevent the spread of disease, viruses, bacteria, and illness.

Often times, an Automated Endoscope Re-processor (AER) is used to dry the reprocessed endoscopes. However, endoscopes have channels with small internal diameters. There may be residual moisture within those channels, even after AER drying, that may provide an environment in which micro-organisms can quickly multiply and potentially be a source to transmit infection to a patient when an endoscopy is performed on that patient.

After endoscope reprocessing, an endoscope is generally disposed within a clean tray and a clean cover can be secured to the perimeter of the tray. The tray can then be loaded into a cart. The endoscope is then transported from a reprocessing room, where it is dried, and then transported back to a procedure room.

Before the reprocessed endoscope is disposed within the tray, if the tray has been previously used and has been contaminated, it must be cleaned to prevent the tray from contaminating the reprocessed endoscope. Trays can be cleaned in a cart washer, where fluid, chemicals and/or heat are applied to the tray in order to wash the tray. However, during tray washing, fluid can accumulate in the tray, making it harder for the tray to dry. If moisture remains in the tray after an endoscope is disposed in the tray, the moisture can increase the likelihood of contaminants developing in the tray and/or the endoscope. Also, depending on the configuration of the tray, it may not be compatible with the cart washer and must instead be cleaned manually. Further, when trays are loaded into the cart washer, often, the trays do not securely engage with the cart washer.

Thus, there is a need to develop a new tray, systems and methods where apertures are disposed on at least a portion of a tray to facilitate drainage of fluid that is captured within the tray during washing. There is also a need to develop a tray and a cart that are compatible with each other, and where the tray maintains a secure engagement with the cart. It would also be beneficial to provide a tray that can be used during the final stages of endoscope reprocessing so that the endoscope can remain in the tray after reprocessing and then transported and stored in the same tray.

SUMMARY

New devices, systems and methods are provided to facilitate drainage of fluids from an endoscope tray when the tray is washed in a cart. The tray and the cart are also provided to store the endoscopes after they are washed. In some embodiments, an endoscope tray is provided. The tray comprises an interior for storage of an endoscope. The interior has an upstanding element having a top surface, and a plurality of apertures disposed on at least a portion of the top surface of the upstanding element to facilitate drainage of fluids.

In some embodiments, an endoscope tray is provided. The tray comprises an interior for storage of an endoscope. The interior has a bottom surface and a sidewall. The bottom surface has a plurality of apertures disposed on at least a portion of the bottom surface to facilitate drainage of fluids, and the sidewall extends about the interior of the endoscope tray and has no apertures.

In some embodiments, an endoscope tray is provided. The tray comprises an interior for storage of an endoscope having an upstanding element having a top surface. A plurality of apertures are disposed on at least a portion of the top surface of the upstanding element to facilitate drainage of fluids. A sidewall and a rim are disposed about the interior of the tray, and a lid is configured to engage the rim.

In some embodiments, a system for storage of an endoscope is provided. The system comprising a tray comprising an interior for storage of the endoscope. The interior has an upstanding element having a top surface. A plurality of apertures are disposed on at least a portion of the top surface of the upstanding element to facilitate drainage of fluids. A sidewall and a rim are disposed about the interior of the tray. A lid is configured to engage the rim, and a liner is configured to engage the rim of the tray.

In some embodiments, a system for storage of an endoscope is provided. The system comprises an endoscope tray comprising an interior for storage of the endoscope. The interior has a bottom surface and a sidewall. The bottom surface has a plurality of apertures disposed on at least a portion of the bottom surface to facilitate drainage of fluids. The sidewall extends about the interior of the tray and has no apertures. A cart comprising a mating surface configured to mate with a corresponding mating surface of the tray to removably hold the endoscope tray in the cart.

In some embodiments, a method of using an endoscope storage tray is provided. The method comprises placing an endoscope within an endoscope tray, the endoscope tray comprising an interior for storage of the endoscope, the interior having an upstanding element having a top surface, and a plurality of apertures disposed on at least a portion of the top surface of the upstanding element to facilitate drainage of fluids.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings.

FIGS. 6 and 6A illustrate a perspective view of the tray of FIG. 1 shown with an endoscope disposed in the interior of the tray. A liner is engaged with the interior of the tray and a cover engages with the tray to enclose the tray. A rigid lid is shown adjacent to the tray and can also engage the tray.

FIG. 27 illustrates a perspective view of a system for storage of an endoscope. The system comprises the tray of FIG. 1 and a cart.

Figure 1:
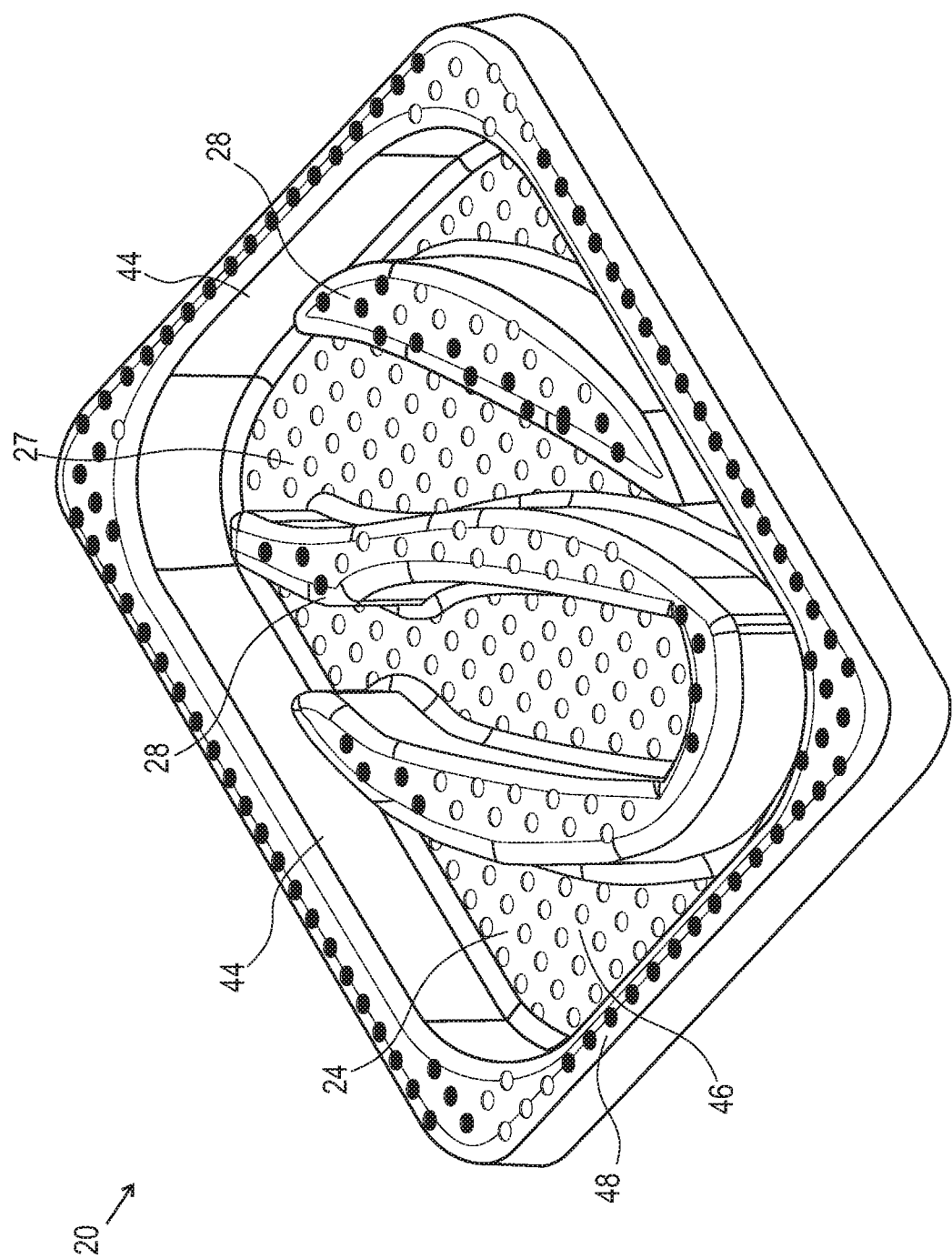
FIG. 1 illustrates a perspective view of an endoscope tray. The tray comprises an interior for storage of an endoscope having an upstanding element having a top surface, and a plurality of apertures disposed on at least a portion of the top surface of the upstanding element to facilitate drainage of fluids.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "outlet" includes one, two, three or more outlets.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

In some embodiments, a tray is provided that is cart washer compatible and that is chemical and heat resistant. In some embodiments, the tray is configured for engagement with cart washer compatible trays and lids. The tray is designed to minimize pooling of fluid within the tray to facilitate drying during a final phase of a reprocessing cycle. In some embodiments, the tray is contoured to allow an endoscope to be retained more securely within an interior of the tray than if the endoscope was retained in a standard tray, thereby minimizing components of the endoscope from being damaged. For example, a light guide connector of the endoscope is heavy and can cause impact damage if it comes into contact with a patient insertion tube of a distal end of an endoscope.

In some embodiments, dimensions of the tray can be sufficient to accommodate substantially all sizes of flexible medical endoscopes in a coiled state without undue stress being applied to the flexible portions of the endoscope. However, the tray can also be sufficiently small to permit it to be easily carried by a person. In some embodiments, the tray is constructed and dimensioned to provide support for the endoscope coiled in a stress-free state.

In some embodiments, the tray is rigid and re-usable and comprises a base having planar and non-planar portions and surrounding sidewalls upstanding therefrom, the tray being formed of a semi-rigid material capable of withstanding repeated disinfection and dimensioned to provide support for a flexible medical endoscope coiled in a stress-free state.

In some embodiments, a shaped tray is provided that is cart washer compatible, has apertures (e.g., perforations) to allow improved automated cleaning, prevents pooling of a fluid in an interior of the tray and improves drying at the end of a cart washer cycle. In some embodiments, the tray is designed to prevent contact of sensitive areas of an endoscope from coming into contact with each other during storage and transportation which prevents damage to the endoscope.

In some embodiments, a lid is provided that engages with the tray and is also cart washer compatible. In some embodiments, the lid does not include apertures. In some embodiments, the lid is self-sealing on an upper surface of the tray. The lid can seal onto the tray by the natural vacuum created when the lid and tray mate. In some embodiments, the lid includes one or more valves, such as an exhaust valve to allow displacement of trapped air, and a release valve to allow pressure to equalize so that the lid can be removed from the tray.

In some embodiments, a shaped base liner is provided configured to engage with an interior of the tray. In some embodiments, the liner contours the interior of the tray and creates a contact engagement. In some embodiments, the tray can engage with a mating surface of a cart to support the tray and secure it to a cart during transportation. In some embodiments, the tray improves storage and transport decontamination.

Tray

Referring to FIGS. 1-6A, an endoscope tray 20 is provided. The tray is configured to store a flexible medical endoscope 22 and to facilitate drainage of fluids that are captured within the tray during tray washing. In some embodiments, the tray is rigid and reusable. In some embodiments, the tray can be formed of a semi-rigid material capable of withstanding repeated disinfection and dimensioned to provide support for the endoscope coiled in a stress-free state.

Figure 4:
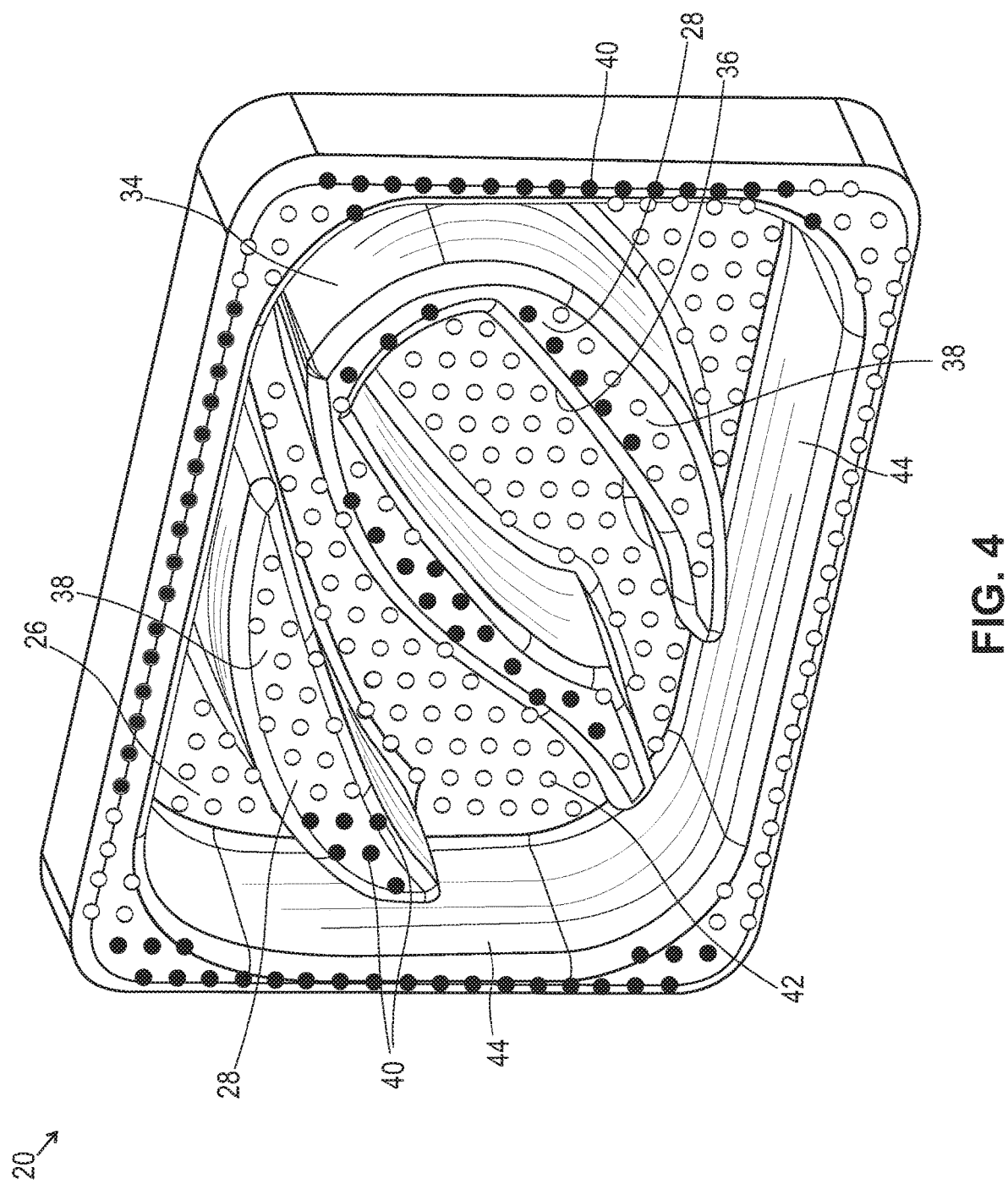
FIG. 4 illustrates a perspective view of the tray.

The tray comprises an interior 24 for storage of the endoscope. The interior defines an inner surface 26 that forms a base or bottom surface 27 that includes an upstanding element 28. The upstanding element is configured to embrace and protect coils 30 of the endoscope without undue stress being applied to the endoscope when stored in the tray. In some embodiments, the interior comprises at least two upstanding elements spaced apart from each other to provide contour and support to at least a portion of the endoscope coiled between all or a portion of the at least two upstanding elements, as shown in FIG. 4.

The interior can define more than one or two upstanding elements. For example, the interior can define 3, 4, 5 or 6 upstanding elements. In some embodiments, at least a portion of the upstanding element can include a curved portion or a side wall 34 and a straight portion or a side wall 36. In some embodiments, each of the side walls of the upstanding element/elements have no apertures.

The upstanding element includes a top surface 38. The top surface includes a plurality of apertures 40 disposed on at least a portion of the top surface of the upstanding element to facilitate drainage of fluids. The apertures can be variously configured and can be circular holes, indents, slits, and/or cutout shapes. In some embodiments, the apertures can be in discrete positions on the top surface, on edges of the top surface, or can be randomly positioned on the top surface.

Figure 2:
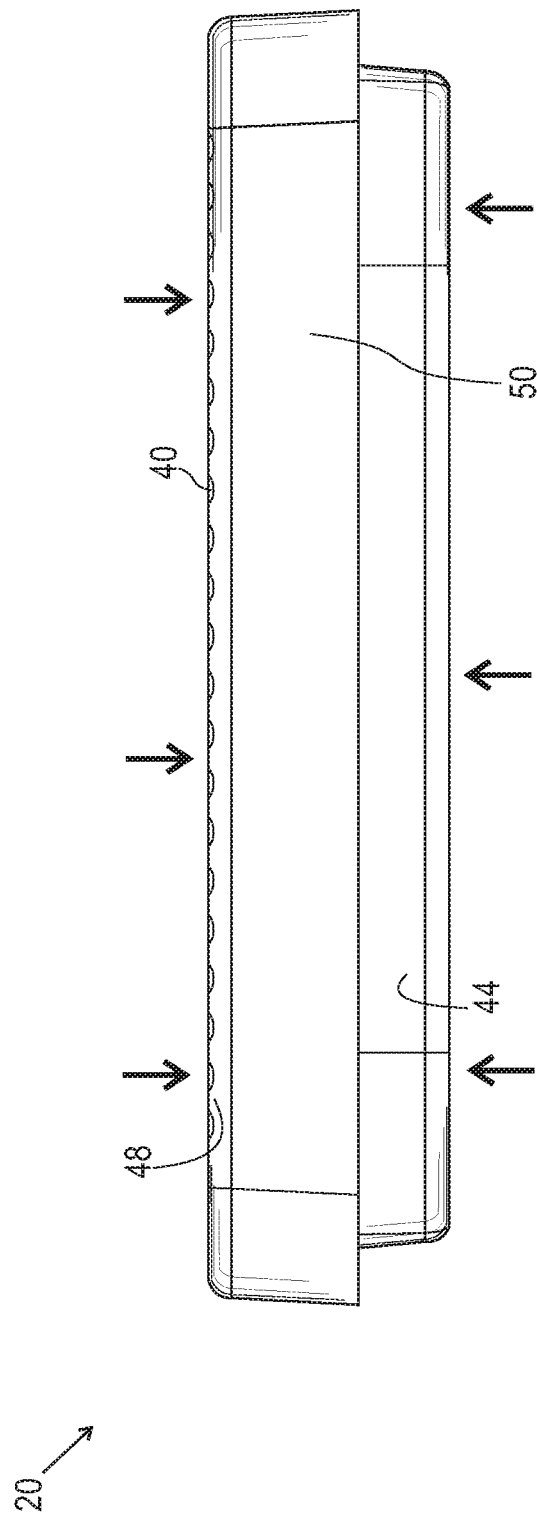
FIG. 2 illustrates a side view of the tray, shown in FIG. 1.

The top surface can include from 1 to about 1000, from 1 to about 500, from 1 to about 250, from 1 to about 100, from 1 to about 75, from 1 to about 50, from 1 to about 25, from 1 to about 20, from 1 to about 15, from 1 to about 10, or from 1 to about 5 apertures on the top surface of the upstanding element. In some embodiments, the top surface can include from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 to about 1000 apertures on the top surface. The apertures are positioned to allow air flow into the tray, as shown in FIG. 2, and allow drainage of fluid and/or moisture from the reprocessed endoscope to be removed from the tray. This is also for trays that are stored in rows and/or are stacked in a cart.

The apertures can have a certain size. For example, the apertures can be from about 1 millimeter (mm) to about 10 mm, from about 1 mm to about 8 mm, from about 1 mm to about 6 mm, from about 1 mm to about 4 mm, and/or from about 1 mm to about 2 mm. In some embodiments, the apertures can be the same size or different sizes. The apertures can be a certain shape, such as, for example, circular, oval, disc, star, rectangular, square, triangular, freeform, semicircular, octagonal, pentagonal, cross, ring, crescent, hexagonal and/or quatrefoil shaped. In some embodiments, the apertures can be the same or different shapes.

Figure 3:
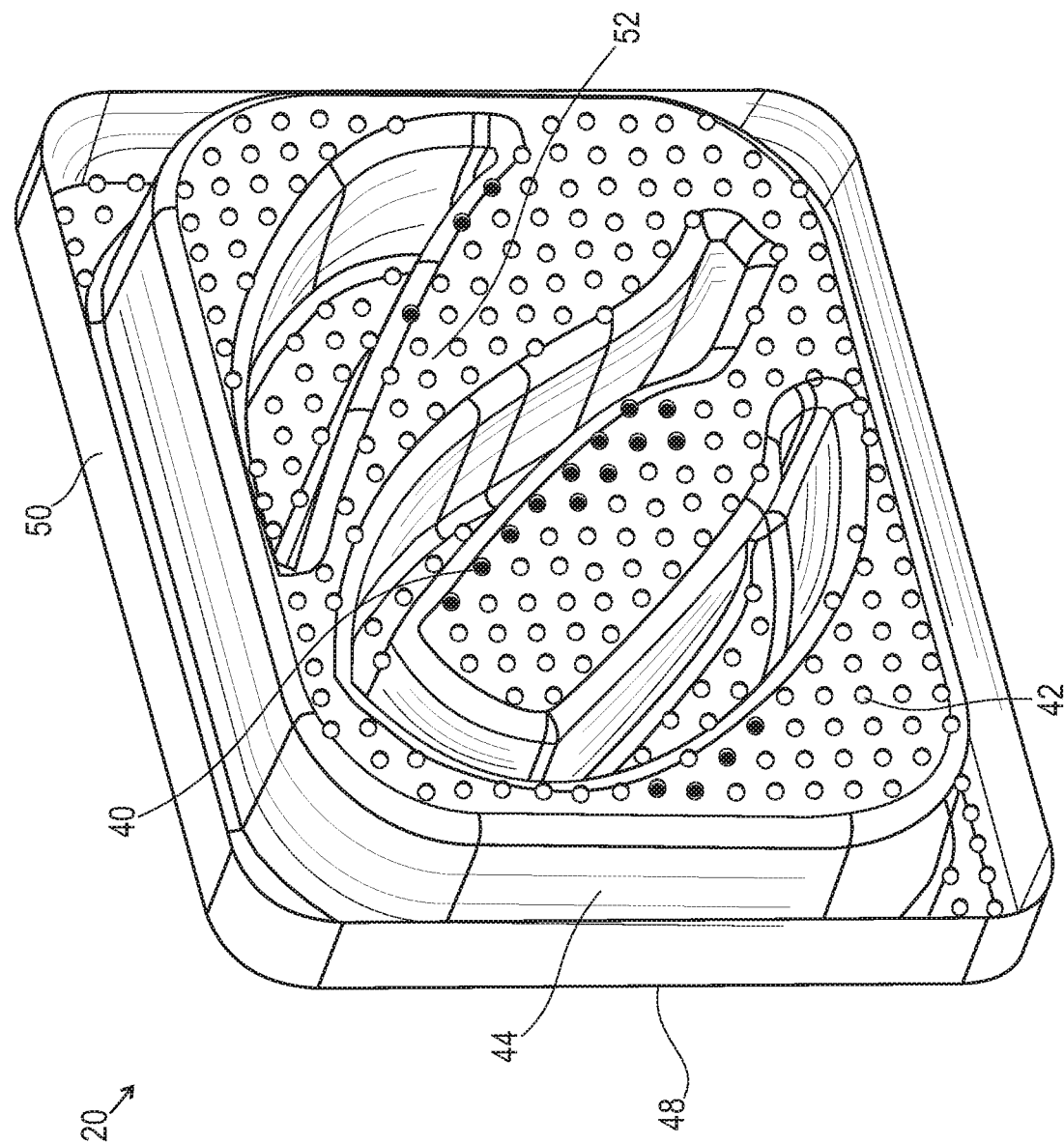
FIG. 3 illustrates a perspective view of the tray of FIG. 1.

The base or bottom surface of the tray, as described above, can include a plurality of apertures disposed thereon. As shown in FIGS. 3 and 4, the apertures can be sealed apertures 42. In some embodiments, the sealed apertures can be punctured manually if a user wishes to drain a tray more quickly.

The base or bottom surface of the tray can include surrounding sidewalls 44 upstanding therefrom. The sidewalls extend about the interior and have no apertures. In some embodiments, the sidewalls are continuous and are monolithic with the base or bottom surface of the tray. In some embodiments, the base or bottom surface includes planar portions 46 and non-planar portions such as the upstanding elements, as described above and shown in FIG. 1. The tray can also include non-planar portions 47 on a portion of the exterior sidewalls or exterior on the base of the tray, as shown in FIG. 6.

The tray can include a rim 48. In some embodiments, the rim includes the plurality of apertures, and the top surface of the at least two upstanding elements align with the rim on a same plane. As shown in FIG. 2, the tray can also include a peripheral lip 50 disposed at least partially around the surrounding sidewalls and extending outwardly therefrom. The tray includes a bottom 52, as shown in FIG. 3. In some embodiments, the bottom of the tray is configured to engage with at least a portion of a cover, as described herein.

Figure 5:
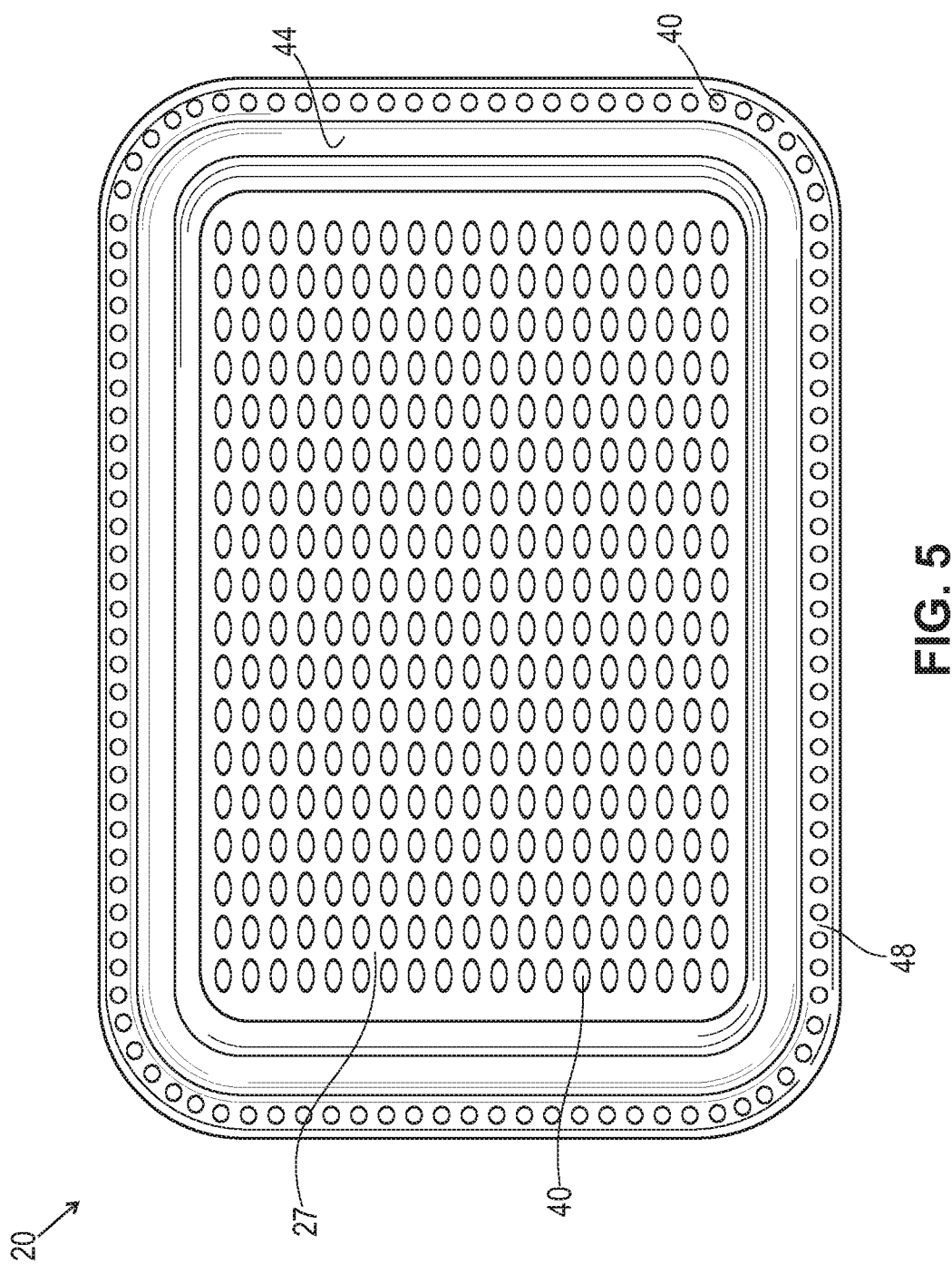
FIG. 5 illustrates a top view of an embodiment of the tray in FIG. 1. In this embodiment, the tray comprises an interior for storage of the endoscope. The interior has a bottom surface and a sidewall. The bottom surface has a plurality of apertures disposed on at least a portion of the bottom surface to facilitate drainage of fluids, and the sidewall extends about the interior of the endoscope tray and has no apertures.

As shown in FIG. 5, the tray alternatively does not include an upstanding element, and the plurality of apertures are disposed on at least a portion of the bottom surface to facilitate drainage of fluids. In some embodiments, the bottom surface of the tray and/or the rim can include the plurality of apertures.

It will be understood that in some embodiments, the all apertures extend completely through the tray to maximize drainage and air flow. In some embodiments, some of the apertures do not extend completely through the tray and there may be a mix of apertures extending completely through and those that do not extend completely through the tray.

The tray can be made from a material such as, for example, a polymeric material. The polymeric material can be thermoplastic and/or is a polycarbonate. For example, the tray can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloropene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof. The tray can also be made from steel, aluminum, paper, bamboo, cork, glass, hemp or any combination thereof.

In some embodiments, the tray can have a certain length, width and height. In some embodiments, the length of the tray can be from about 16 to about 34 inches, the width can be from about 12 to about 24 inches and the height can be from about 3 to about 8 inches. In some embodiments, the length of the tray can be from about 16, 18, 20, 22, 24, 26, 28, 30, 32 to about 34 inches, the width of the tray can be from about 12, 14, 16, 18, 20, 22 to about 24 inches, and the height of the tray can be from about 3, 4, 5, 6, 7 to about 8 inches.

The components of the tray, individually or collectively, may also be fabricated from a heterogeneous material such as a combination of two or more of the above-described materials. The tray as described herein may be constructed of a suitable biocompatible material to impart various desirable characteristics, such as rigidity, and resilience.

Components of the tray can also be made from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), plastic (e.g., polycarbonates), ABS, MABS, or the like or combinations thereof.

Storage System

Referring to FIGS. 6-27, an endoscope storage system 53 is provided. The system comprises tray 20, as described above. In some embodiments, the system comprises a rigid lid 54 configured to engage with the rim of the tray to seal the tray closed, as shown in FIGS. 6 and 6A. In some embodiments, the lid can self-seal with the rim of the tray by a natural vacuum created when the lid is mated with the tray. In some embodiments, the lid comprises at least one valve 56 to facilitate sealing the tray closed. In some embodiments, the at least one valve can have similar features to the one-way valve found and described in U.S. Publication No. 2015/0259122, assigned to Cantel (UK) Limited. This publication is herein incorporated by reference.

In some embodiments, the at least one valve is an exhaust valve and a release valve to seal the lid with the tray, as shown in FIG. 6. In some embodiments, the at least one valve is a non-return valve/one-way valve, as shown in FIGS. 7 to 7D. When the lid is engaged with the tray, the at least one valve communicates with airspace within the interior of the tray.

In some embodiments, the at least one valve includes a valve that allows fluid (liquid or gas) to flow through it in only one direction thereby preventing any backward flow. Conventional one-way valves can be used that are provided in the lid that allow fluid (liquid or gas) to flow through it in only one direction thereby preventing any backward flow. The one-way valve can be controlled by the pressure applied to the valve and will open when the pressure inside and the pressure outside of the valve are different. This can be placed on after the moisture or fluid is removed by the apertures.

In some embodiments, the at least one valve comprises an outlet 58 configured to release air flowing from the interior of the tray, an inlet 60 to allow air from the interior to enter the at least one valve when suction is applied, and a seal 62 that allows only air to enter the inlet for release out of the outlet, as shown in FIG. 7. The seal is disposed between the inlet and the outlet and is a movable barrier configured to reduce or prevent contaminants from entering into the interior of the tray.

Figure 7A:
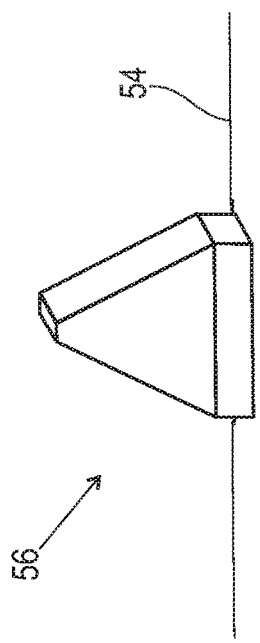
FIGS. 7, 7A, 7B, 7C and 7D illustrate embodiments of a valve that is attached to the lid of FIGS. 6 and 6A. The valve facilitates the sealing of the lid to the tray.
Figure 7:
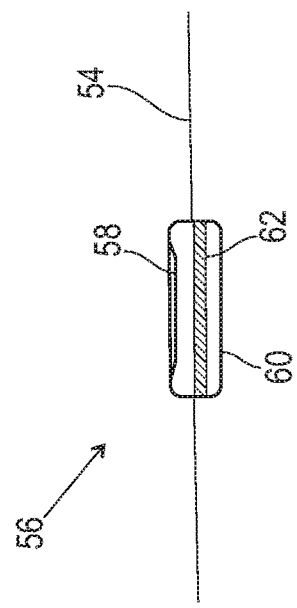
Figure 7C:
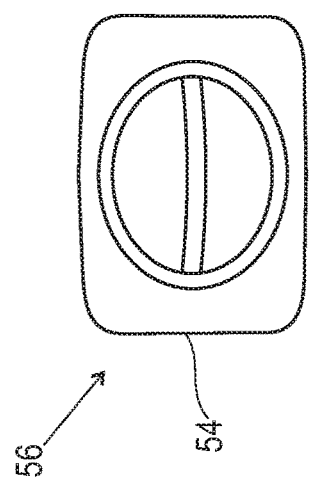
Figure 7B:
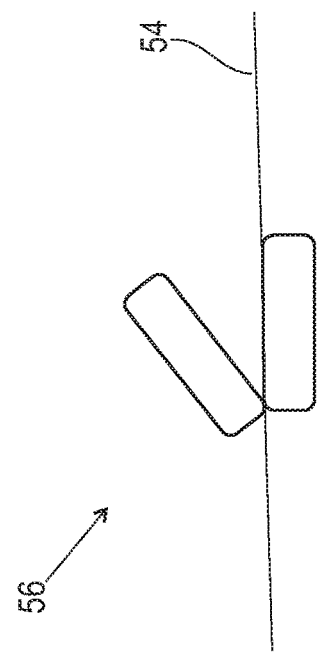
Figure 7D:
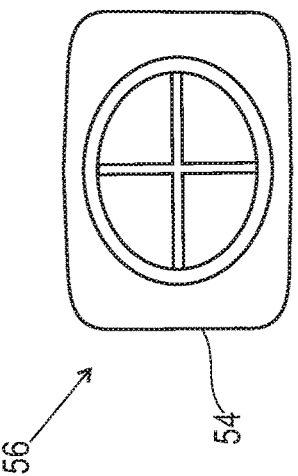

In some embodiments, the at least one valve can be a pressure valve or a degassing valve, as shown in FIG. 7, a duckbill valve, as shown in FIG. 7A, a flap valve, as shown in FIG. 7B, a valve comprising a single slit diaphragm, as shown in FIG. 7C or a valve comprising a double or cross shaped slit diaphragm, as shown in FIG. 7D.

In some embodiments, the at least one valve is a controlling device for the passage of suction in one direction and is controlled by the suction applied to the at least one valve by a suction device (not shown), such as a vacuum. For example, the at least one valve will be closed when no suction is provided, however, when suction is provided, the suction will force the at least one valve to open, thereby releasing air from the interior of the tray. It is to be understood that the at least one valve is a valve that allows the passage of air in one direction and that the at least one valve will open when the pressure or suction outside of the interior is less than the pressure inside of the interior. The at least one valve will close when pressure difference between the outside of the tray and the interior is not significantly different. The pressure difference, in some embodiments, will aid in removing moisture or fluid from the endoscope.

In some embodiments, the at least one valve can be positioned within or on the lid in a few ways. For example, the at least one valve can be centrally attached to the lid or it can be attached to an edge of the lid. In some embodiments, the at least one valve is monolithically formed with the lid or is attached to the lid by an adhesive, a friction fitting and/or tape.

In some embodiments, the system includes a liner 64. The liner is configured to engage with the interior of the tray and the endoscope, as shown in FIG. 6. In some embodiments, the liner engages contours of the interior and rim of the tray. In some embodiments, the liner is similar to the liner found and described in U.S. Pat. No. 6,749,063, assigned to Cantel (UK) Limited. This patent herein is incorporated by reference. The liner can be disposable and can be substantially impermeable to fluids.

In some embodiments, the tray interior and portions of the exterior of the tray can be engaged by the liner. The liner can be made of a flexibly deformable material substantially impermeable to fluids.

In some embodiments, the disposable liner contacts the bottom surface of the tray and at least partially encloses the reprocessed endoscope. In some embodiments, the liner is a disposable single use liner that may be sterile or unsterile.

In some embodiments, the disposable liner is configured to temporarily line the entirety of the interior compartment of the tray and prevents the endoscope from having direct contact with the interior of the tray. In some embodiments, the liner prevents moisture from the reprocessed endoscope from contacting the tray and when the tray is used repeatedly, it prevents or reduces contamination from one endoscope to the next endoscope.

The tray whether it is lined or not lined can be temporarily covered with a disposable cover 66, as shown in FIGS. 6, 8 and 9-9B. In some embodiments, the disposable cover at least partially encloses or encloses the reprocessed endoscope and the tray. In some embodiments, the cover is a disposable single use cover that may be sterile or unsterile. In some embodiments, the cover can be similar to the cover found and described in U.S. Pat. No. 6,749,063, assigned to Cantel (UK) Limited. This patent is herein incorporated by reference.

The cover for the endoscope storage tray can comprise a flexibly deformable sheet material substantially impermeable to fluids, the flexibly deformable sheet material configured to be temporarily secured to the endoscope storage tray so as to cover at least an interior of the endoscope storage tray. The cover can engage with the rim and/or the lip of the tray to temporarily secure the cover to the tray.

Figure 8:
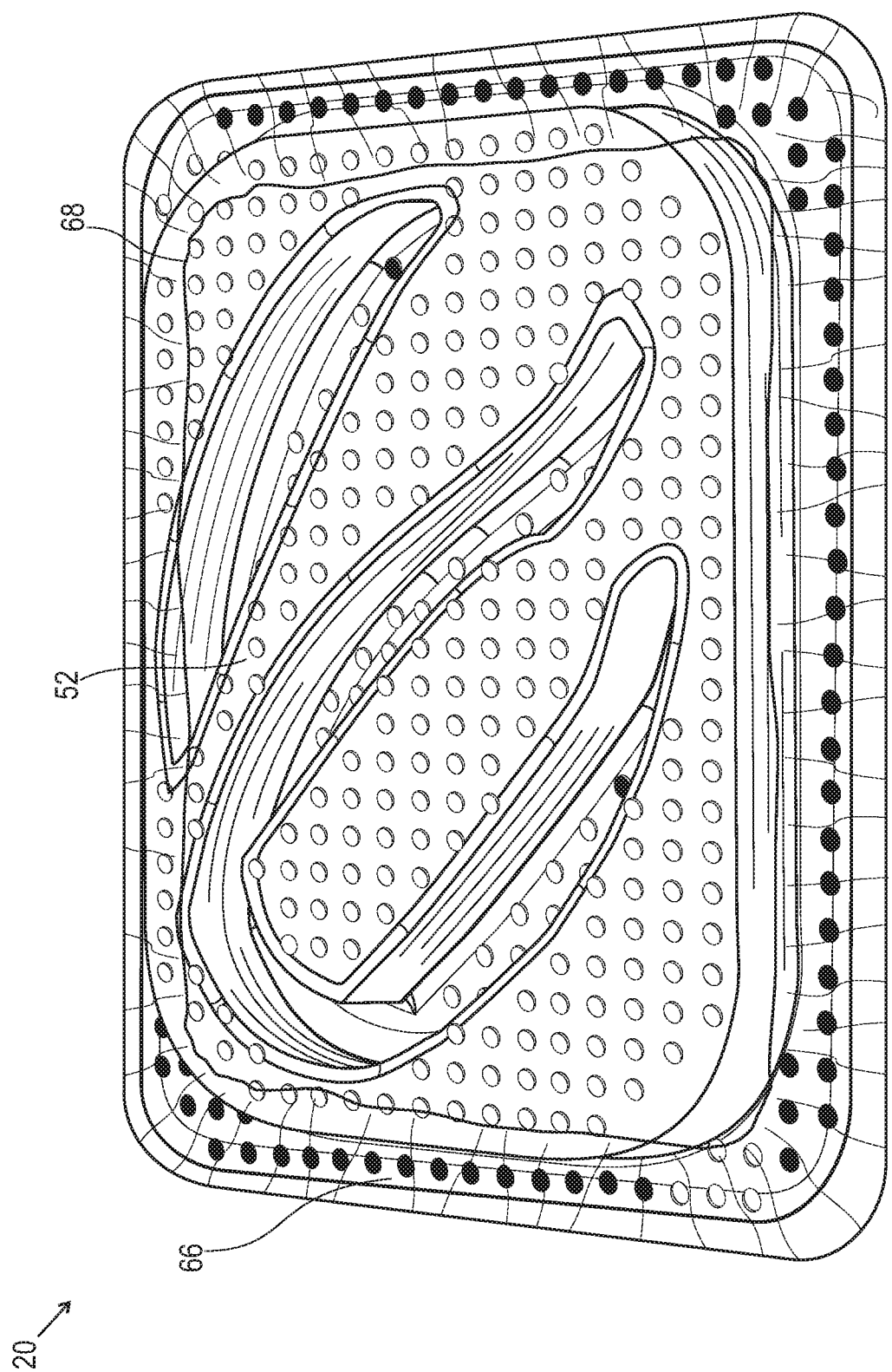
FIG. 8 illustrates a bottom perspective view of the tray and an embodiment of the cover of FIG. 6. In this embodiment, the cover engages and partially encloses the tray with an elastic portion.
Figure 9:
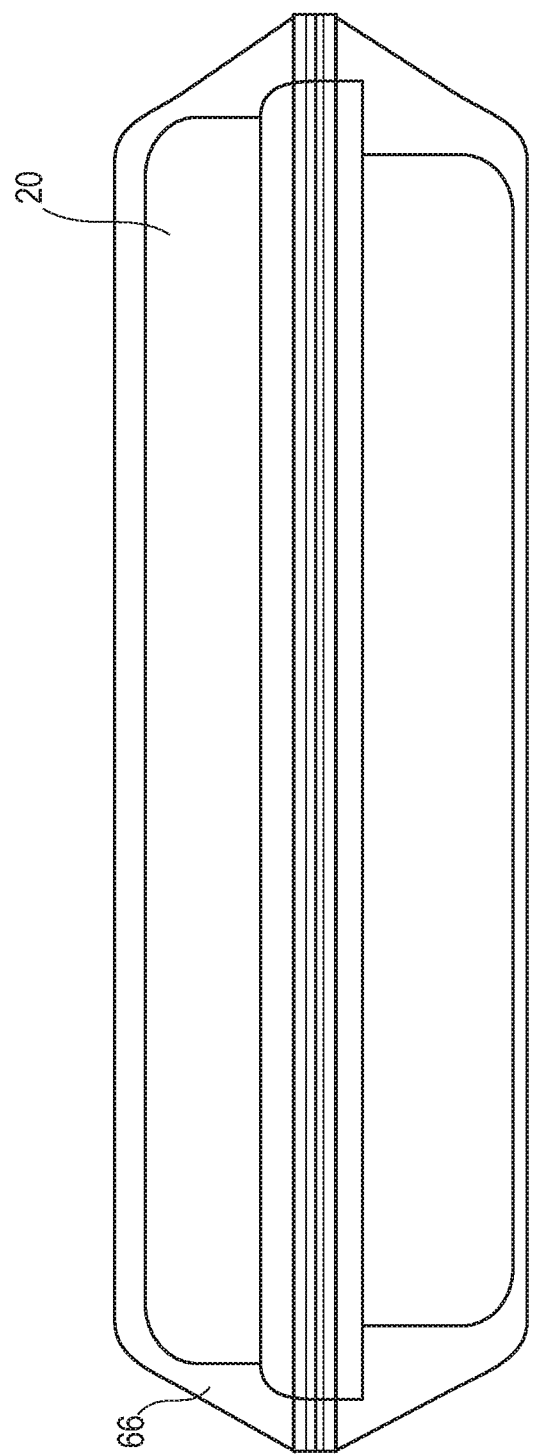
FIG. 9 illustrates a side view of the tray and an embodiment of the cover of FIG. 6. In this embodiment, the cover is in a bag configuration.
Figure 9B:
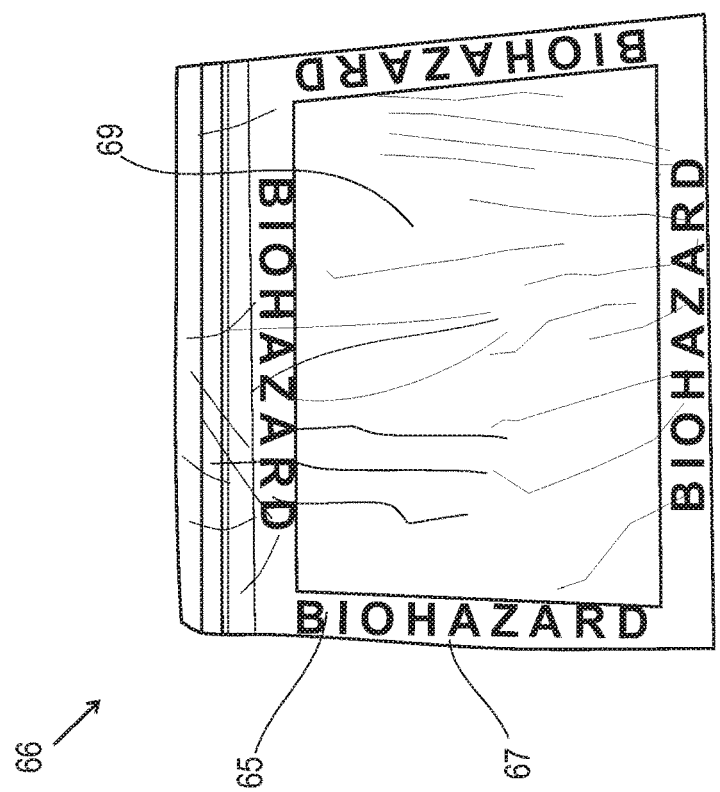
FIG. 9B illustrates a top view of the cover of FIG. 9A shown on its reversible red/biohazard side.
Figure 9A:
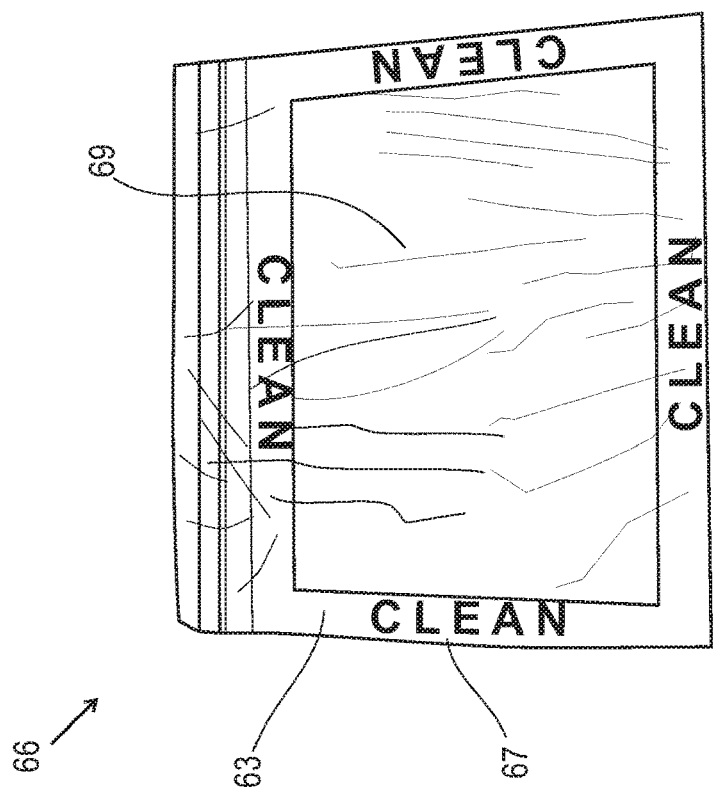
FIG. 9A illustrates a top view of the cover of FIG. 9 in a reversible configuration. In this configuration, the cover is shown on its reversible green/clean side.

In some embodiments, the cover can be in a sheet (FIGS. 6 and 8) or a bag/pouch configuration (FIGS. 9-9B). For example, when the cover is in a bag/pouch configuration, the cover can be a reversible pouch, as shown in FIGS. 9A and 9B. The reversable bag/pouch is configured to entirely enclose the tray. In some embodiments, the reversible bag/pouch can have a clean/green colored side 63 and a biohazard/red side 65. The clean/green side can have indicia 67 in the form of a word, words and/or symbols. For example, the indicia can be the word "CLEAN". In some embodiments, the biohazard/red side can have indicia 115 in the form of a word, words and/or symbols. For example, the indicia can be the word "BIOHAZARD". When the tray is inserted/engaged into a cart, as described below, and the clean/green side is facing upward, this can indicate to a user that the endoscope is clean and ready for use. When the tray is inserted/engaged into the cart and the biohazard/red side is facing upward, this can indicate to a user that the endoscope is contaminated, should not be used and that the endoscope needs to be reprocessed. In some embodiments, the reversible bag/pouch can have a clear/transparent viewing window 69 in the center of each side of the bag/pouch. In some embodiments, the reversible bag/pouch can be sealed by a zipper.

In some embodiments, the cover engages and partially encloses the tray with an elastic portion 68, as shown in FIG. 8. In some embodiments, the sheet or bag configuration can have a rectangular shape to correspond with the shape of the tray but other cover shapes are contemplated depending on tray shape. These shapes include oval, square, circular or the like. In some embodiments, the cover can be temporarily secured to the rim of the tray, and/or the bottom of the tray.

The cover can be manufactured in different colors such as in a green or a clear color to indicate that the endoscope is clean and ready for use. A red color, in some embodiments, could indicate that the tray should not be used and the endoscope should be cleaned. Alternative colors can be selected such as blue, pink, yellow, orange, brown or black to indicate the status of the endoscope. In some embodiments, the cover can be reversible and a different color can be used on the inner surface than on the outer surface of the cover.

The system includes a cart 70, as shown in FIGS. 10-26. The cart is configured to assist in the transportation and/or storage of one or more of the trays that store one or more endoscopes. It is to be understood that the cart is defined as a mobile storage unit. However, a cabinet which is defined as a static or stationary storage unit can alternatively be used. The cart can also be an endoscope washing and/or drying cart. The cart includes a housing 72. The housing includes a first side panel 74 and a second side panel 76, as shown in FIG. 11. The first and the second side panels are in a parallel configuration relative to each other and are spaced apart at a certain distance, such as, for example, a distance that is greater than the width of the trays. Each of the side panels include a first support 78, a second support 80, a rail 82 and a base 84. The first and the second support are in a parallel configuration relative to each other and the rail and the base are in a parallel configuration relative to each other.

The rail extends from a first end 86 to a second end 88. The first end fixedly engages with the first support by an engagement means 90, such as a bracket, screw, adhesive and/or soldering. In some embodiments, the first end and the first support are manufactured fused together and are monolithic. The first end and the first support, in some embodiments, form a 45-degree angle where they engage. The second end fixedly engages with the second support by engagement means 90. In some embodiments, the second end and the second support are manufactured fused together and are monolithic. The second end and the second support form a 45-degree angle where they engage. The base extends between a proximal end 92 and a distal end 94, and includes an upper surface 96 and a lower surface 98. The base fixedly engages with an end 100 of the first support at the upper surface and toward the proximal end. The base and the end of the first support can form a 45-degree angle where they engage. The base fixedly engages with an end 102 of the second support at the upper surface and toward the distal end. The base and the end of the second support can form a 45-degree angle where they engage. The base and end 100 of the first support and end 102 of the second support can fixedly engage via engagement means, similar to those described above with regard to engagement means 90. A first brace 101 and a second brace 103 fixedly engage the bases.

In some embodiments, each rail of each of the side panels collectively form a runner assembly 104. The runner assembly is configured for engaging with the tray and allows for the movement of the tray in a forward and backward direction once removably mounted on the runner assembly. Each rail includes an inner side 106 that includes a slot 108. A bearing 110 can be positioned within the slot to facilitate retractable movement of an arm 112. In some embodiments, the bearing and the arm movably engage relative to each other.

Figure 10:
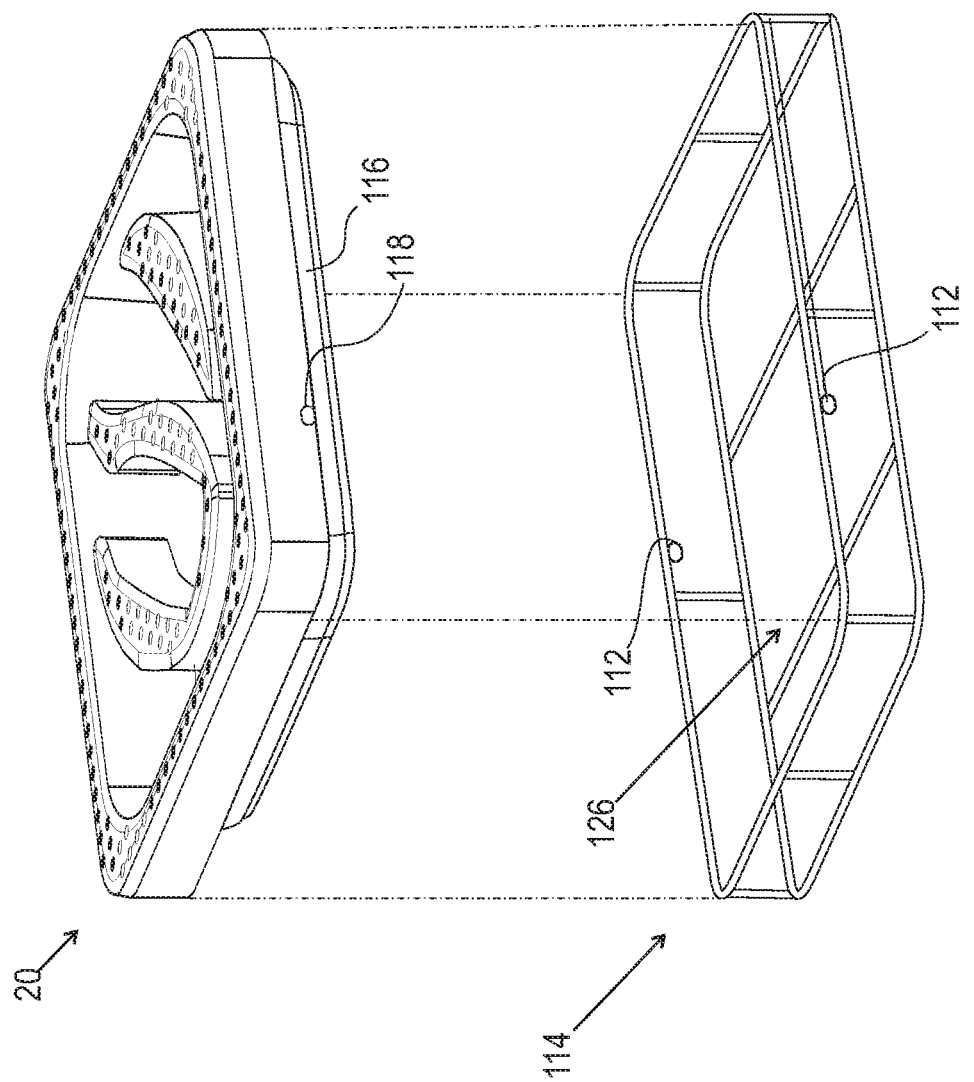
FIG. 10 illustrates a perspective view of the tray of FIG. 1 and a mating surface in the form of a frame. The frame is a component of a cart and is configured to mate with a corresponding mating surface of the tray to removably hold the tray into the cart.
Figure 11:
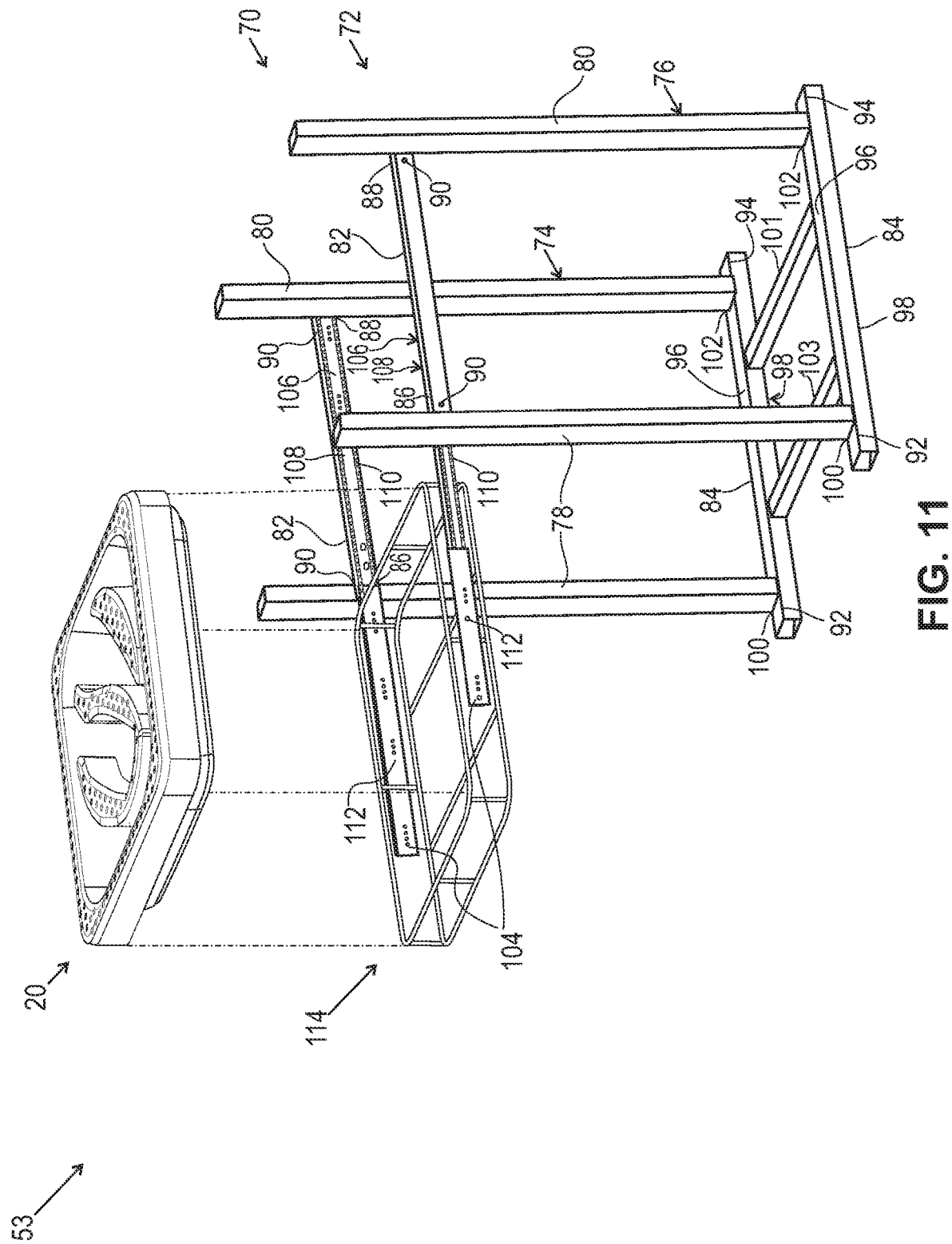
FIG. 11 illustrates a perspective view of a system for storage of an endoscope. The system comprises the tray and frame of FIG. 10 and a cart.

As shown in FIG. 10, the cart includes a mating surface, such as a frame 114. The frame can be variously configured, as shown in FIGS. 10, 13, 16 and 19. The frame is configured to mate with a corresponding mating surface 116 of the tray (FIG. 10) to removably hold the endoscope tray in the cart. The tray removably engages the frame, and the cart allows the tray containing the endoscope to be transported to a patient for use. In some embodiments, the mating surface of the tray corresponds to a particular frame (e.g., mating surface) of the cart and the frame (e.g., mating surface) of the cart corresponds to a particular mating surface of the tray.

Figure 13:
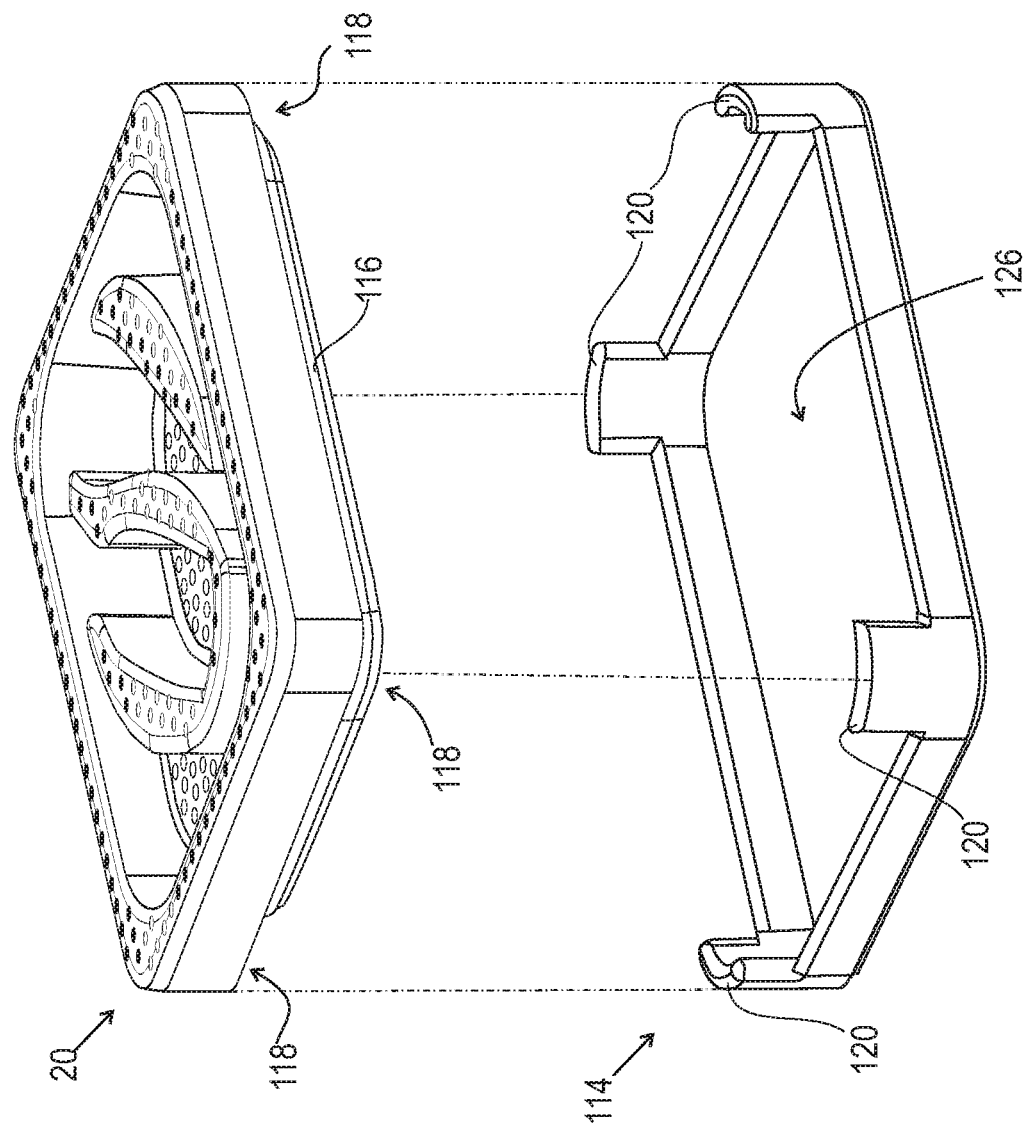
FIG. 13 illustrates a perspective view of the tray of FIG. 1 and a mating surface in the form of a frame. The frame is a component of a cart and is configured to mate with a corresponding mating surface of the tray to removably hold the tray into the cart.
Figure 16:
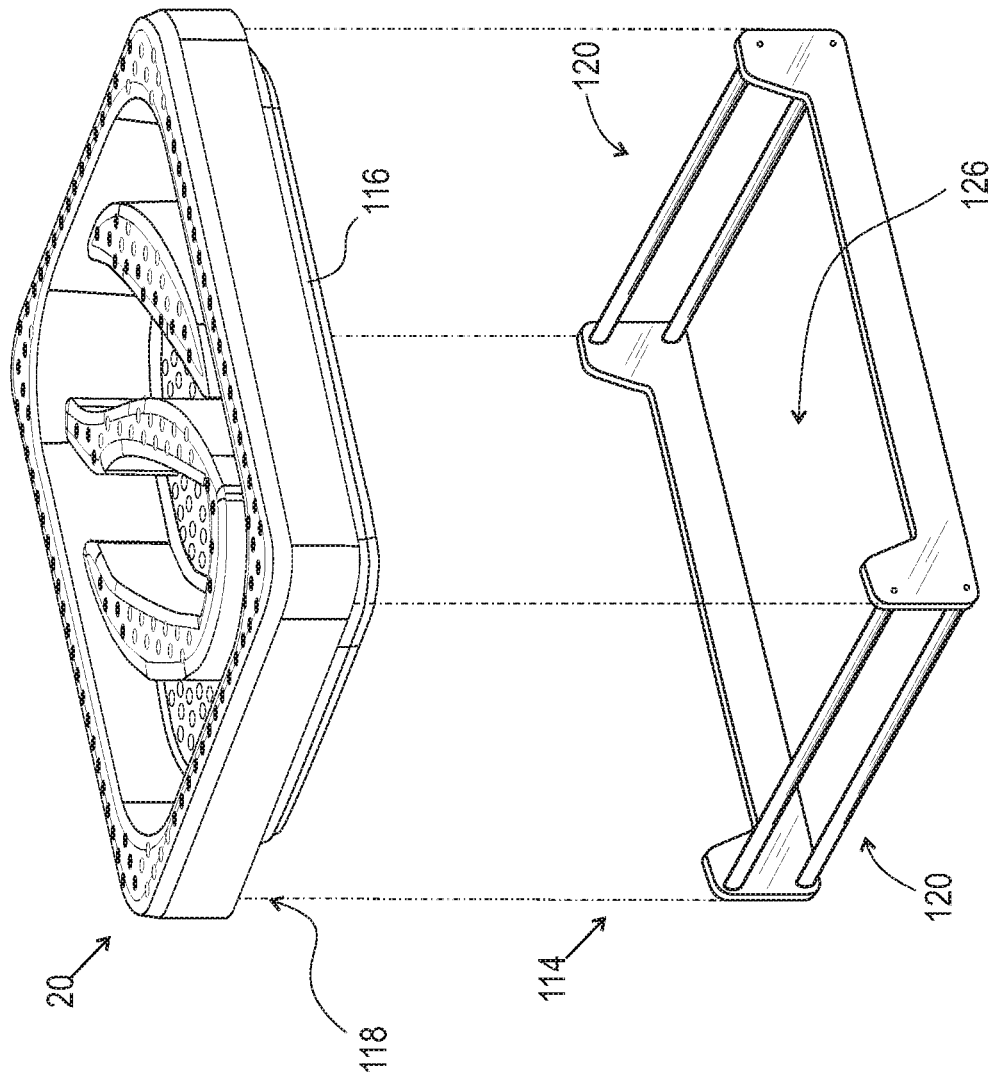
FIG. 16 illustrates a perspective view of the tray of FIG. 1 and a mating surface in the form of a frame. The frame is a component of a cart and is configured to mate with a corresponding mating surface of the tray to removably hold the tray into the cart.
Figure 19:
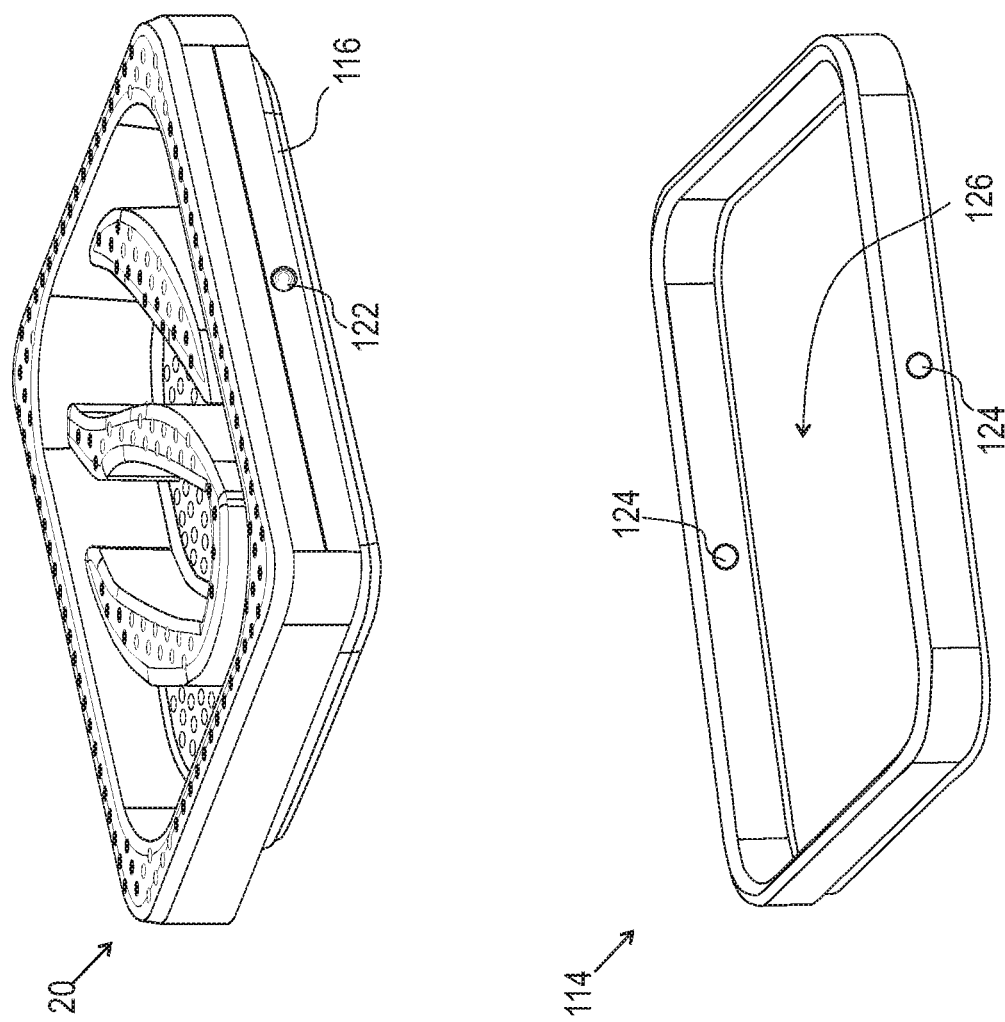
FIG. 19 illustrates a perspective view of the tray of FIG. 1 and a mating surface in the form of a frame. The frame is a component of a cart and is configured to mate with a corresponding mating surface of the tray to removably hold the tray into the cart.

In some embodiments, the mating surface of the tray can be at least a portion of the sidewalls of the tray, the peripheral lip and/or the rim of the tray. The mating surface of the tray and the frame (e.g., mating surface) of the cart can also temporarily lock. For example, the mating surface of the tray can include one or more recesses 118 that mates with one or more projections 120 on the frame, as shown in FIGS. 10, 13 and 16. Alternatively, the mating surface of the tray can include one or more projections 122 that mates with one or more recesses 124 on the frame, as shown in FIG. 19. In some embodiments, the tray and the frame can be in locked engagement through one or more grooves, teeth, indents, tongues, peaks, valleys, ribs, flanges, dimples, slots, or a combination thereof disposed on the mating surface of the tray and the frame. The locked engagement can include, but is not limited to a friction fit, pressure it, or male/female engagement.

Figure 12:
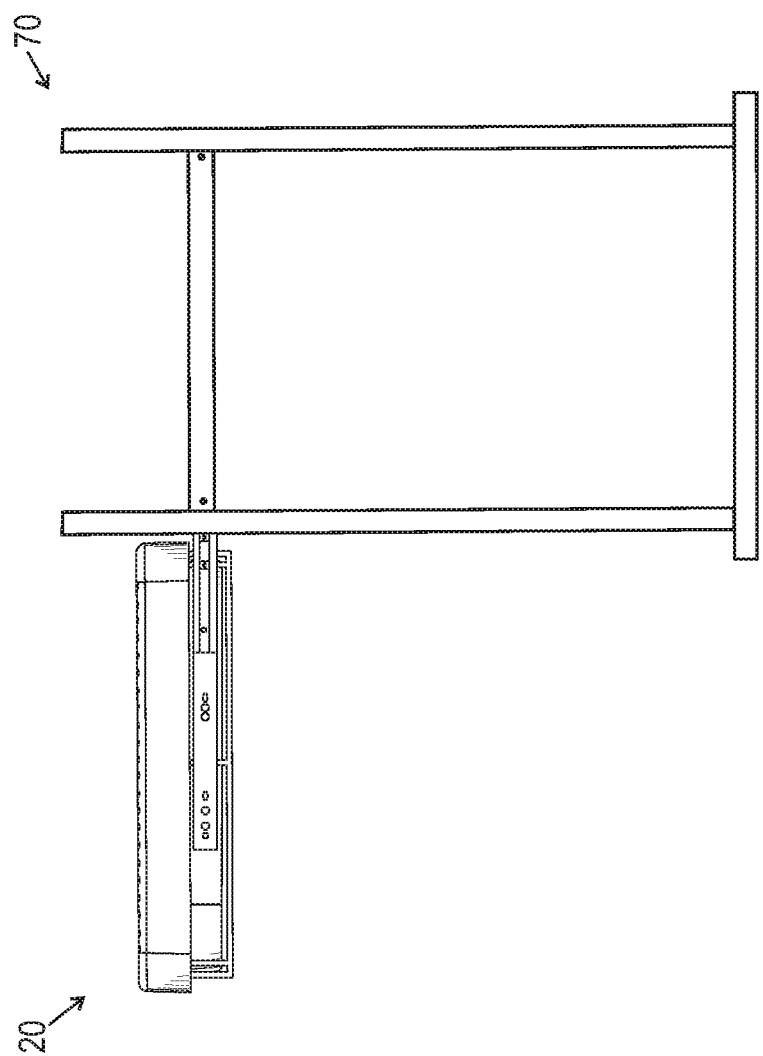
FIG. 12 illustrates a side view of the system of FIG. 11.
Figure 14:
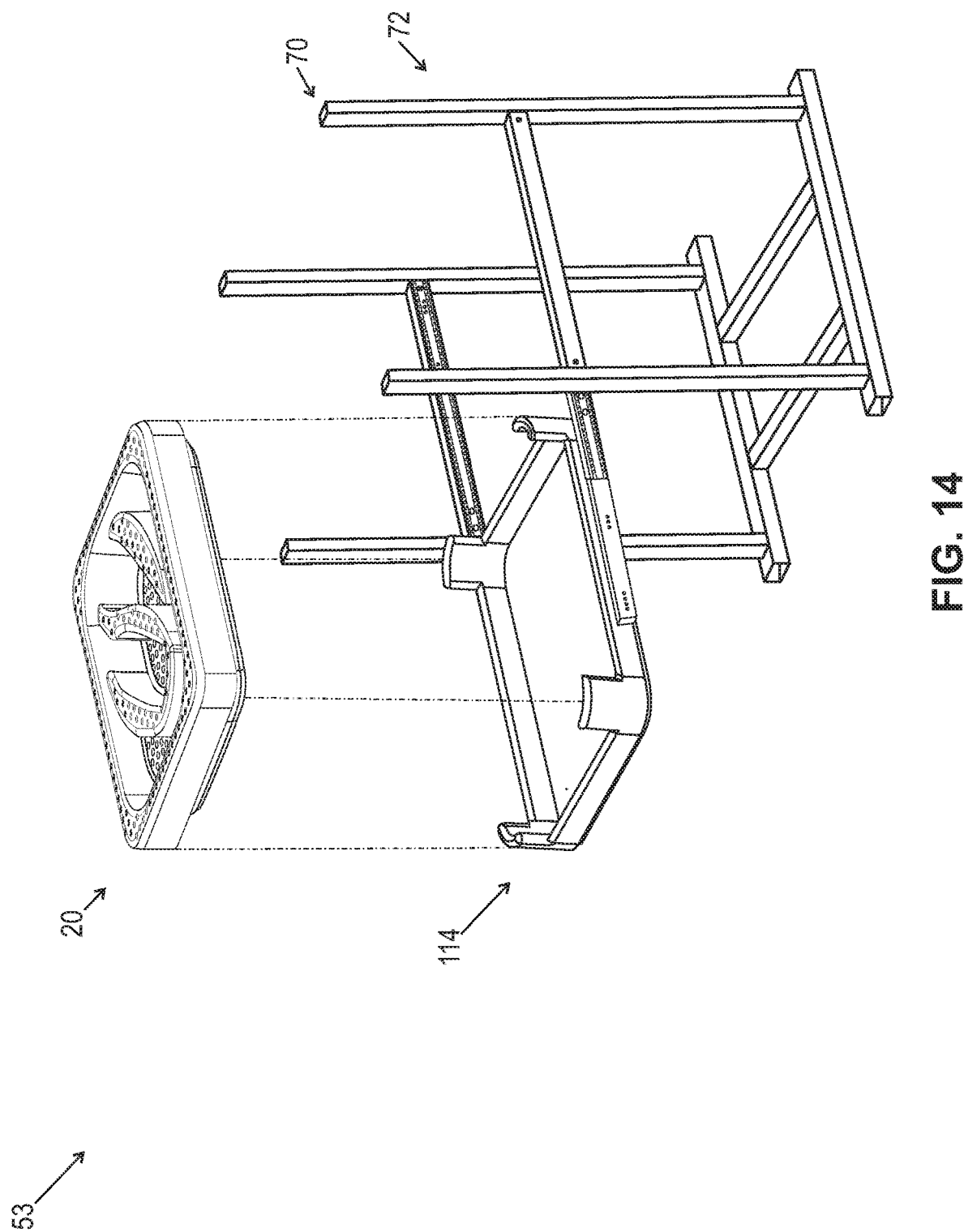
FIG. 14 illustrates a perspective view of a system for storage of an endoscope. The system comprises the tray and frame of FIG. 13 and a cart.
Figure 15:
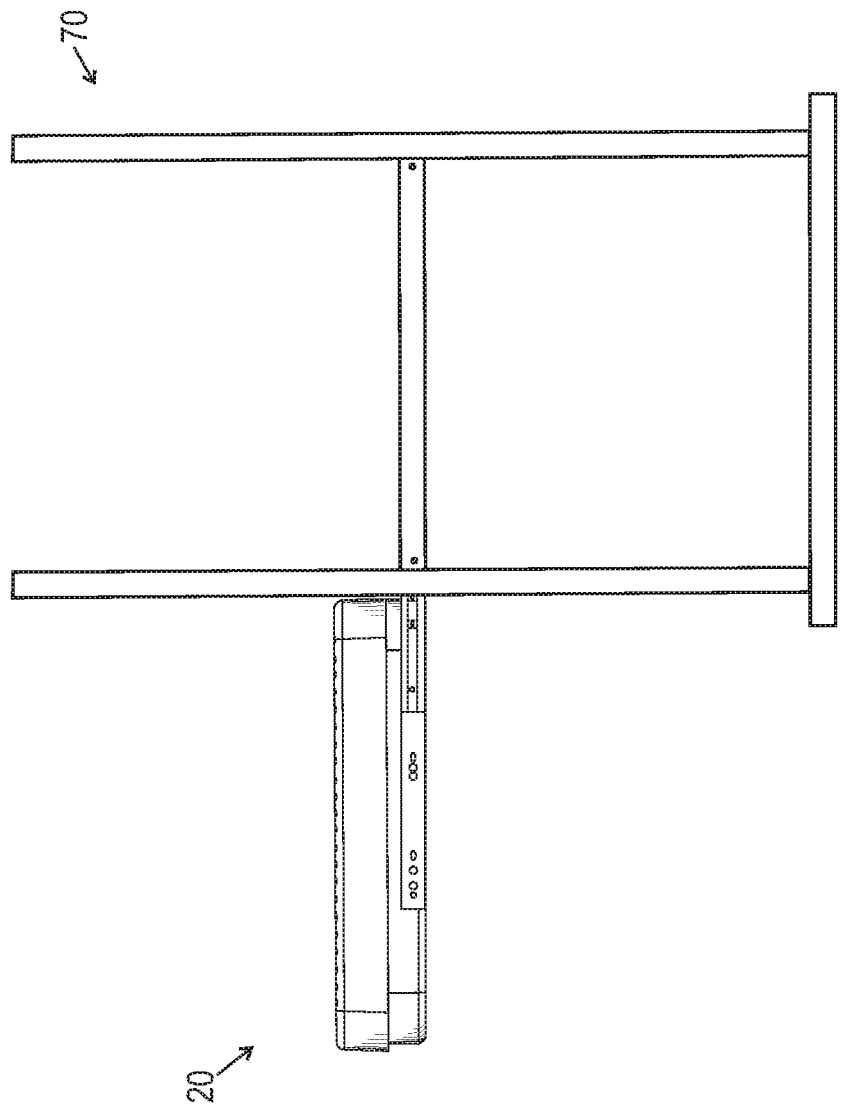
FIG. 15 illustrates a side view of the system of FIG. 14.
Figure 17:
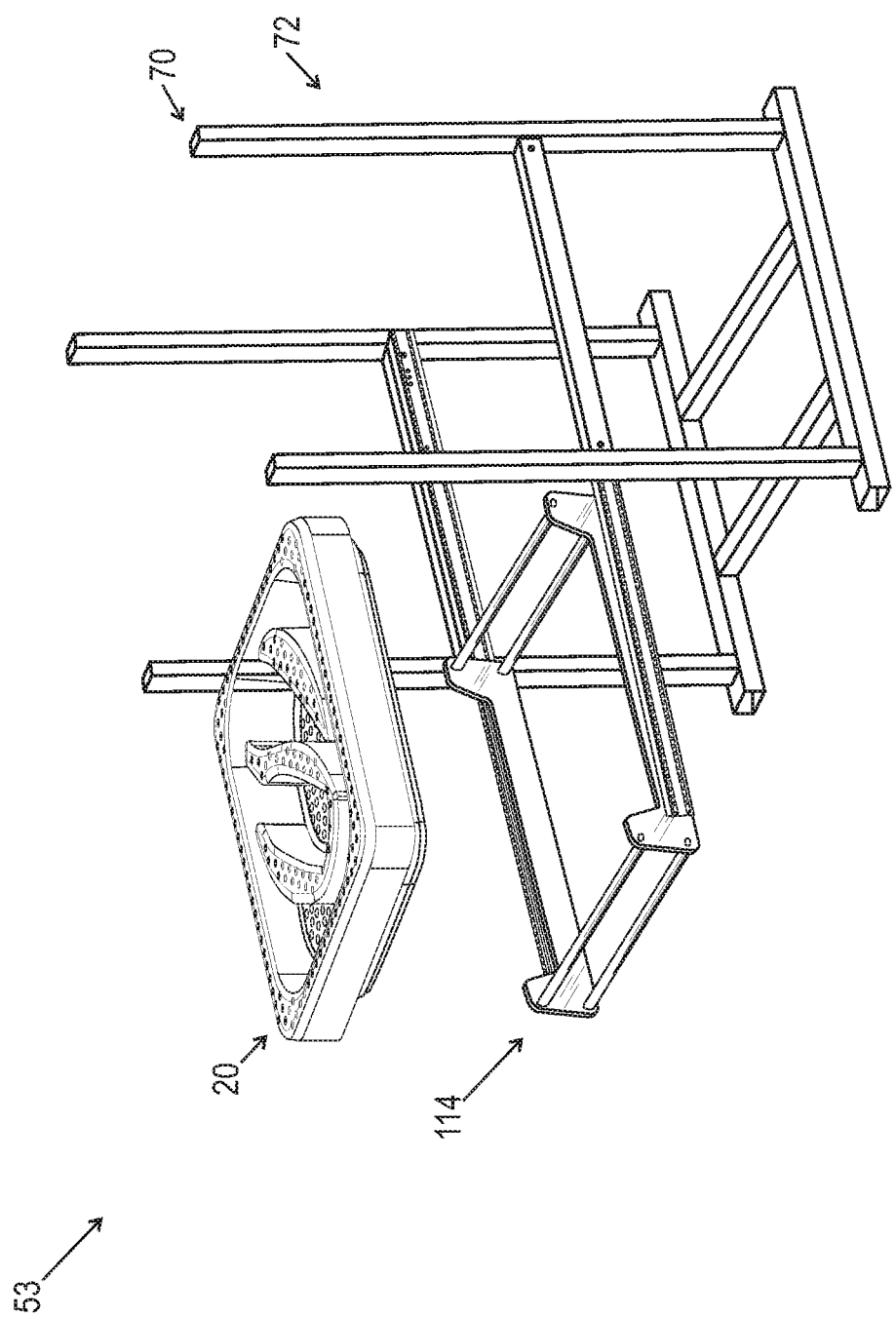
FIG. 17 illustrates a perspective view of a system for storage of an endoscope. The system comprises the tray and frame of FIG. 16 and a cart.
Figure 18:
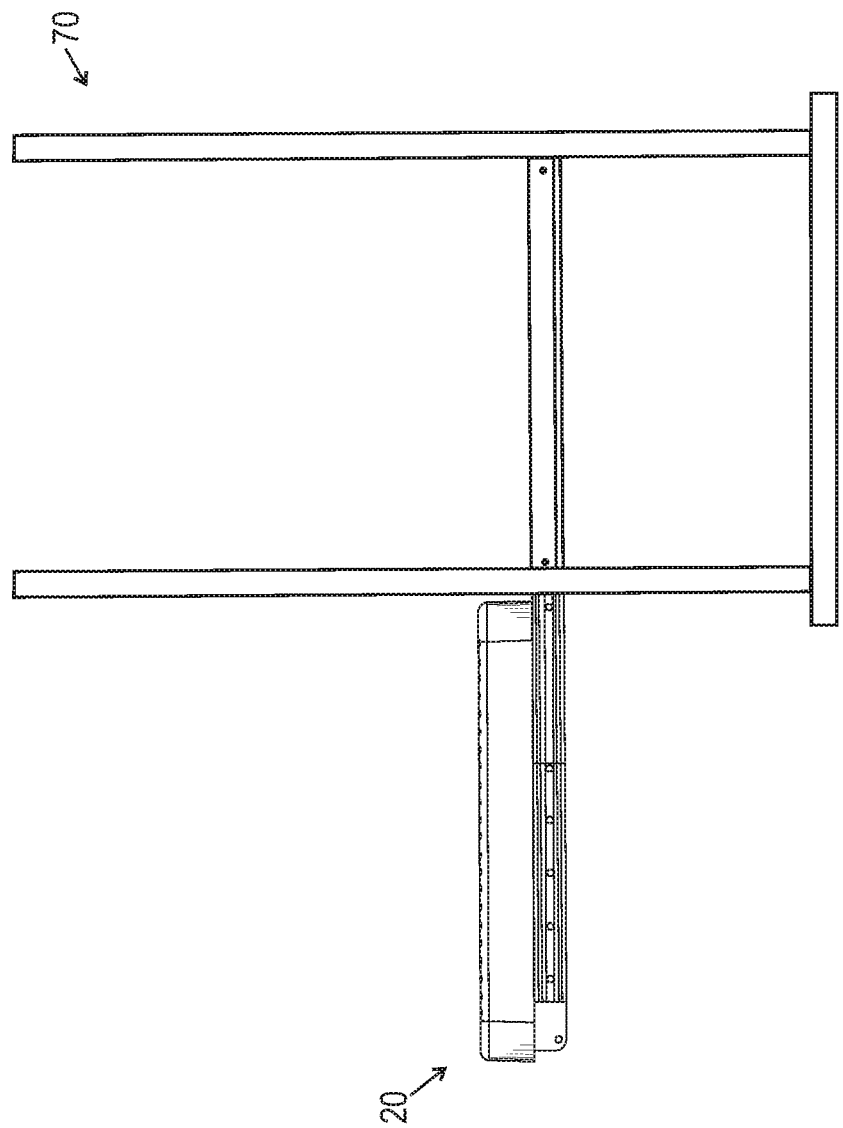
FIG. 18 illustrates a side view of the system of FIG. 17.
Figure 20:
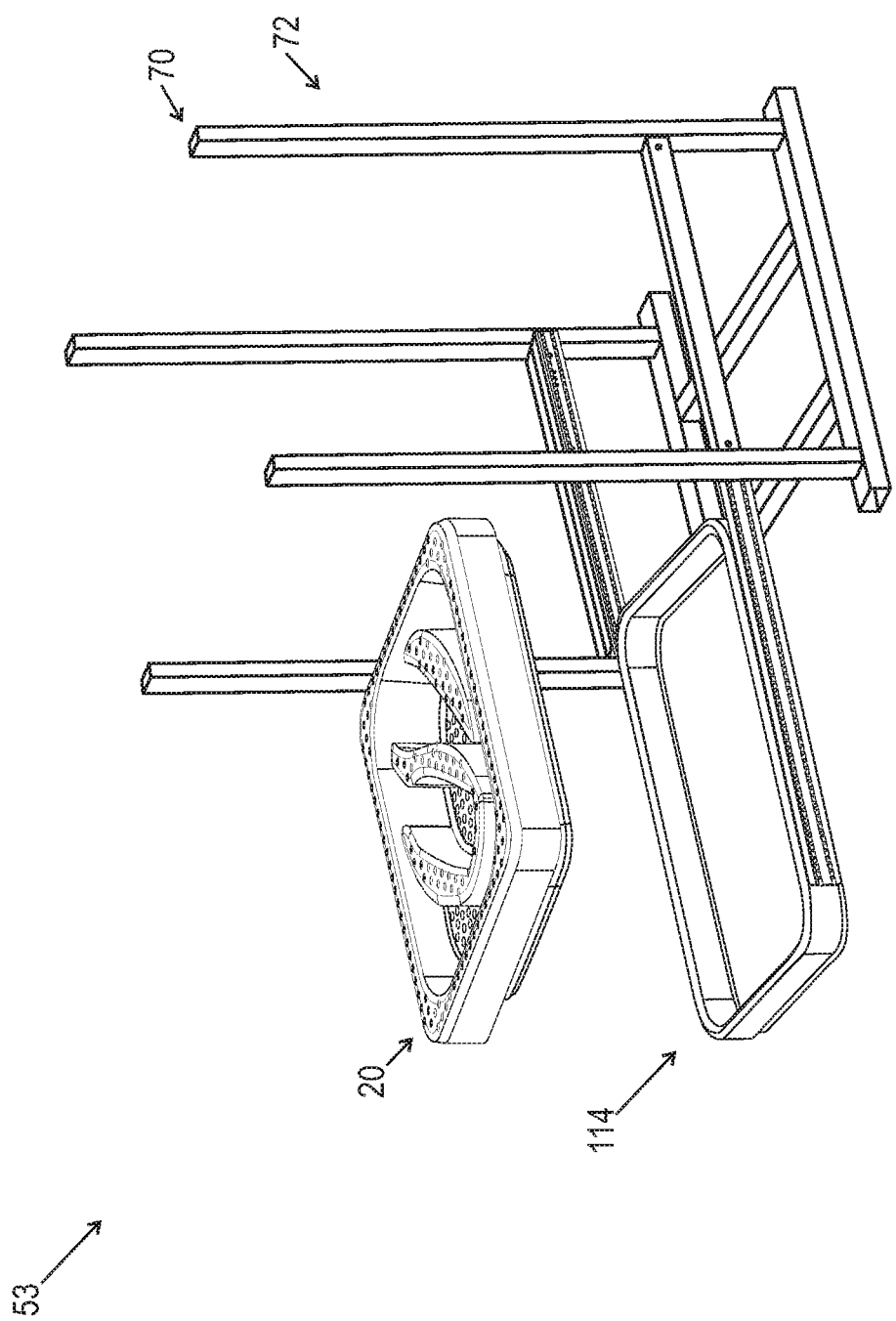
FIG. 20 illustrates a perspective view of a system for storage of an endoscope. The system comprises the tray and frame of FIG. 19 and a cart.
Figure 21:
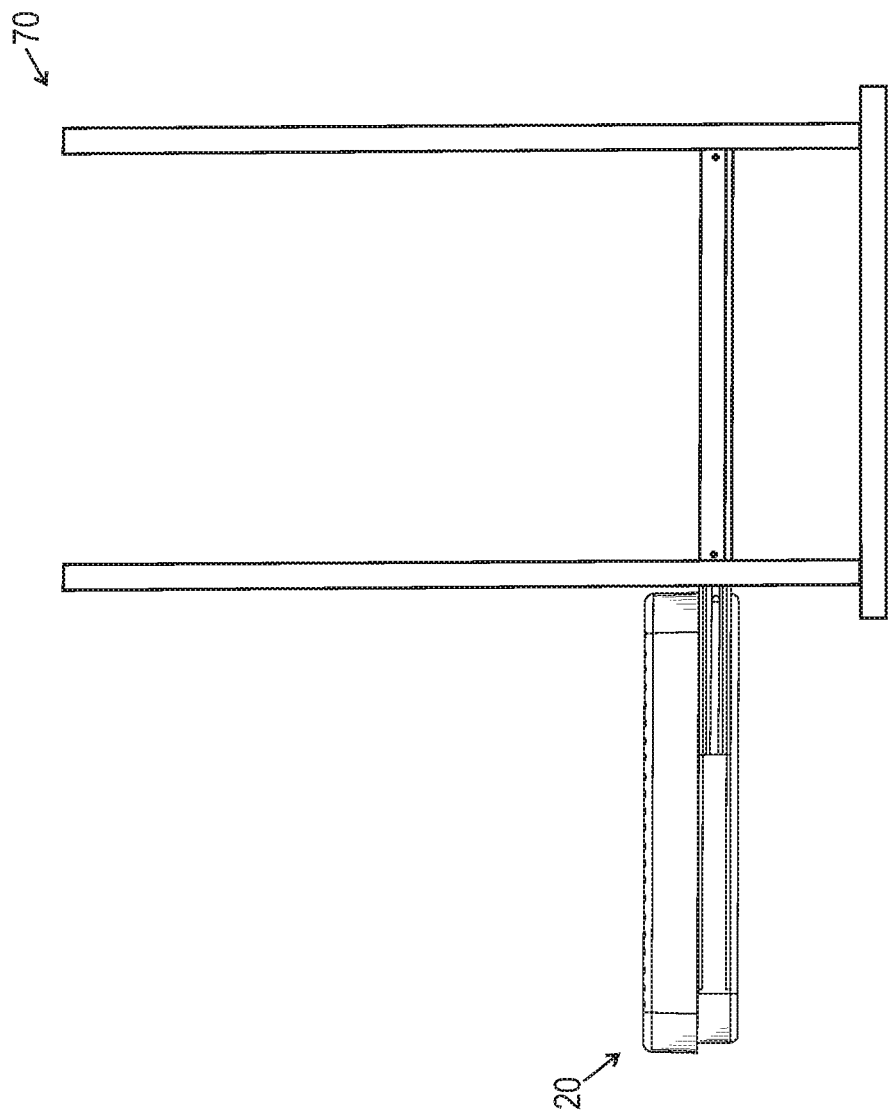
FIG. 21 illustrates a side view of the system of FIG. 20.

The frame can be fixedly or removably engaged with the runner assembly. In some embodiments, the frame can be variously configured. For example, the frame can be in a basket configuration as shown in FIGS. 10-12, where the mating surface of the tray is the peripheral lip and side wall; a solid mount with bracketed edges configuration as shown in FIGS. 13-15, where the mating surface of the tray are portions of the peripheral lip and the tray has a locked engagement with the frame projections; a railed configuration as shown in FIGS. 16-18, where the mating surface of the tray are portions of the peripheral lip and the tray has a locked engagement with the rail projections; and a low profile solid mount as shown in FIGS. 19-21 where the mating surface of the tray are the sidewalls and the peripheral lip.

Figure 22:
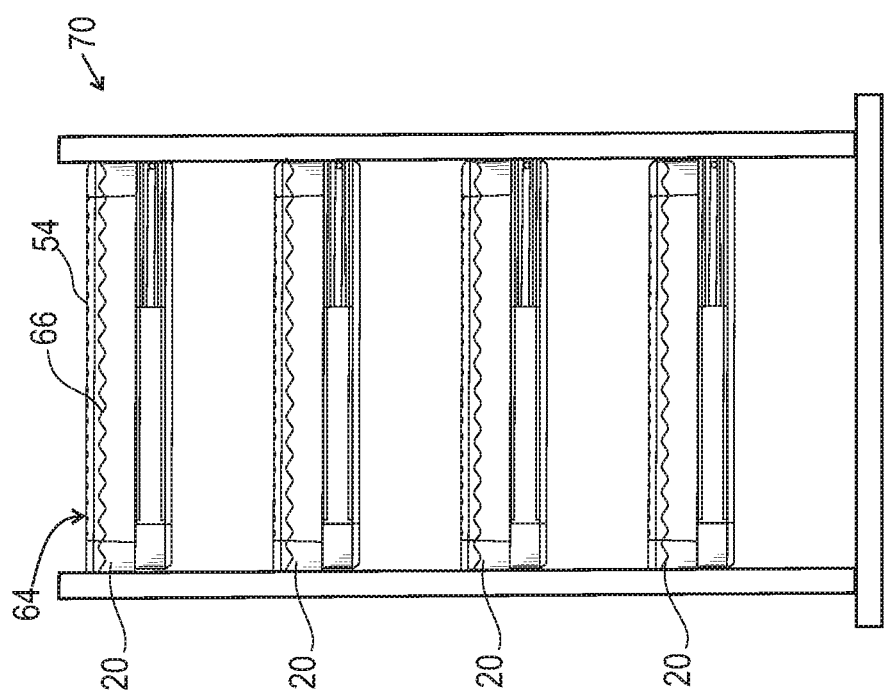
FIG. 22 illustrates a side view of the system of FIG. 11, where multiple trays are stacked vertically within the cart.

The cart can be configured to utilize all of the frames of FIGS. 10-21 in a single cart. In some embodiments, one or all of the frame embodiments can be in a stacked configuration within the cart, as shown in FIG. 22. One or more trays can also be stacked in the cart and disposed with lids, covers and/or liners.

Figure 24:
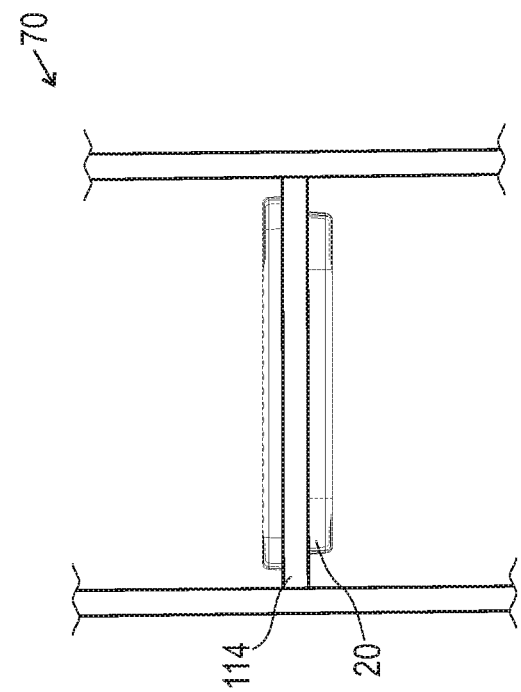
FIG. 24 illustrates a partial front view of the cart of FIG. 11 disposed in the frame of FIG. 23, and the tray of FIG. 1 is in a nested configuration with the frame.
Figure 23:
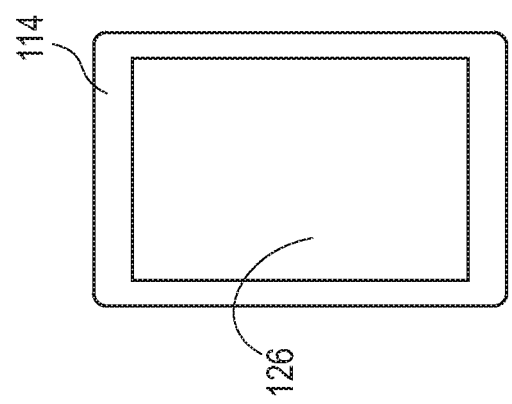
FIG. 23 illustrates a top view of a mating surface of the cart of FIG. 11 in the form of a frame. The frame is a component of the cart and is configured to mate with a corresponding mating surface of the tray to removably hold the tray into the cart. A pocket is defined in the frame and the tray is configured to nest within the pocket as the pocket is configured to receive and hold at least a portion of the exterior of the tray. In this embodiment, a perimeter of the frame is larger than at least a portion of the tray.
Figure 26:
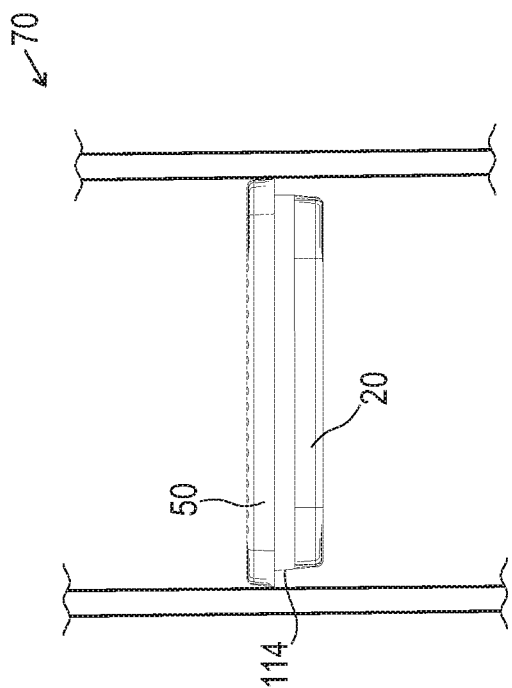
FIG. 26 illustrates a partial front view of the cart of FIG. 10 disposed with the frame of FIG. 25 and the tray of FIG. 1 is in a nested configuration with the frame.
Figure 25:
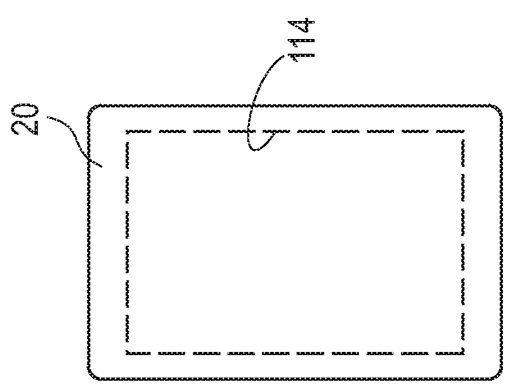
FIG. 25 illustrates a top partially phantom view of a mating surface of the cart of FIG. 11 in the form of a frame engaged with a tray of FIG. 1. The frame is a component of the cart and is configured to mate with a corresponding mating surface of the tray to removably hold the tray into the cart. A pocket is defined in the tray and the tray is configured to nest within the pocket. In this embodiment, the perimeter of the tray is larger than the frame.

The frames can include pockets 126 that are configured for portions of the tray to nest within. The perimeter of the tray, in some embodiments, is smaller than the perimeter of the frame so that the tray nests within the frame, as shown in FIGS. 23 and 24. When the perimeter of the tray is smaller than the perimeter of the frame, there is no tray rim or lip overhang. The perimeter of the tray, in some embodiments, is larger than the perimeter of the frame so that the tray nests within the frame, as shown in FIGS. 25 and 26. When the perimeter of the tray is larger than the perimeter of the frame, the rim or lip of the tray will overhang relative to the frame.

The system can alternatively include a cart 128, as shown in FIG. 27. The cart is configured for storage and/or transportation of the trays. The cart comprises a housing 130. The housing includes opposing side walls 132, 134 and top and bottom walls 136, 138. The cart can be in a rectangular configuration. An interior 140 of the housing comprises one or a plurality of slots 142, each configured to slidably receive the tray. The slots are transverse relative to the opposing side walls. Each slot is defined by ledges 144, 146 that are in parallel orientation relative to each other. The cart can comprise one or more slots, such as 1 to about 12 slots.

In some embodiments, the bottom wall includes an exterior surface 148 that attaches to a plurality of wheels 150, such as caster wheels. The cart can include 4 or more wheels disposed at corners of the exterior surface. The cart can be washed and can be heat and chemical resistant.

The tray can be configured to nest in a specific row in the cart. In this way, a tray cannot be used in a different cart or a different row in the cart. Therefore, a tray that does not have apertures on the bottom surface of the tray, on at least a portion of the top surface of one or more of the upstanding elements, and/or on the rim of the tray would not be able to be used in that cart. Further, specific trays and specific carts can be tailored for specific endoscope suites in a medical facility and can be tailored for patient specific use.

It is to be understood that the tray engaged with the lid, liner and/or the cover and disposed with the cart for storage and/or transportation can reduce the number of receptacles used for endoscope reprocessing and delivery.

The cart can be made from various materials, including, but not limited to metals, such as for example, stainless steel alloys, commercially pure titanium, titanium alloys, Grade 5 titanium, cobalt-chrome alloys, or combinations thereof. In some embodiments, the cart can be made from thermoplastic materials and/or the materials described above with regard to the tray. In some embodiments, the cart are configured to be heat and chemical resistant.

In some embodiments, contaminants can include, but are not limited to, biological contaminants such as microorganisms including bacteria, viruses, yeasts, molds and parasites; air borne contaminants such as airborne microbes; and/or chemical contaminants. In some embodiments, bacterial can include, but is not limited to *Escherichia coli, Klebsiella species, Enterobacter* species, enterococci, *Pseudomonas aeruginosa* and *Salmonella* species.

Methods and Kits

A method of using an endoscope storage tray is provided. The method comprises placing an endoscope within an endoscope tray, the endoscope tray comprising an interior for storage of the endoscope, the interior having an upstanding element having a top surface, and a plurality of apertures disposed on at least a portion of the top surface of the upstanding element to facilitate drainage of fluids. It is to be understood that the tray is tray 20 described above with regard to FIGS. 1-6A.

In some embodiments, the interior comprises at least two upstanding elements spaced apart from each other to provide support for a flexible medical endoscope coiled between all or a portion of the at least two upstanding elements. In some embodiments, the upstanding elements contour portions of the endoscope. In some embodiments, a rigid lid engages the tray. In some embodiments, a disposable liner engages with the interior of the tray.

In some embodiments, components of the system described above may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the components of the system may be formed by 3D printing. The terms "three-dimensional printing system," "three-dimensional printer," and "printing," describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. In some embodiments, components of the system may be color coded to signify various properties.

Components of the system may be sterilizable. In various embodiments, one or more components of the system are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the system. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the system, including, but not limited to, gas sterilization, such as, for example, with ethylene oxide or steam sterilization.

In various embodiments, a kit or system is provided that may include additional parts along with the tray combined together to be used with the cart. The kit may include the tray in a first compartment. A second compartment may include the cover. A third compartment may include the liner. A fourth compartment may include the lid. A fifth compartment may include cleaning solutions, gloves and other procedural supplies for performing cleaning of the endoscope, as well as an instruction booklet or notification of a website where instructions for using the kit or system can be located. Each component of the system or kit may be separately packaged in a plastic pouch. A cover of the kit may include illustrations of the use of the cover and a clear plastic cover may be placed over the compartments to maintain sterility.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. An endoscope storage tray comprising an interior for storage of an endoscope, the interior having an upstanding element having a top surface; a plurality of apertures disposed on at least a portion of the top surface of the upstanding element; a bottom surface also having a plurality of apertures disposed thereon; a sidewall and a rim disposed about the interior of the tray; and a lid comprising no apertures and at least one valve and configured to engage the rim, wherein the endoscope storage tray is constructed of a polymeric material wherein the at least one valve is an exhaust valve and a release valve.

2. The endoscope tray of claim 1, wherein the sidewall does not have a plurality of apertures.

3. The endoscope tray of claim 1, wherein the rim includes a plurality of apertures.

4. The endoscope tray of claim 1, wherein the endoscope tray is configured to engage the lid to seal the endoscope tray closed.

5. The endoscope tray of claim 1, wherein the endoscope tray comprises a liner configured to engage with the interior of the endoscope tray.

6. The endoscope tray of claim 1, wherein the endoscope tray comprises a cover configured to enclose or partially enclose the endoscope tray.

7. The endoscope tray of claim 6, wherein the cover is in a sheet or a bag configuration.

8. The endoscope tray of claim 6, wherein the cover engages and partially encloses the endoscope tray with an elastic portion.

9. A system for storage of an endoscope, the system comprising a tray comprising an interior for storage of the endoscope, the interior having an upstanding element having a top surface; a plurality of apertures disposed on at least a portion of the top surface of the upstanding element; a sidewall and a rim disposed about the interior of the tray; a lid comprising no apertures and at least one valve comprising an exhaust valve and a release valve to seal the lid with the tray; the lid configured to engage the rim; and a liner configured to engage the rim of the tray.

10. The system of claim 9, wherein the interior comprises at least two upstanding elements spaced apart from each other to provide support for a flexible medical endoscope coiled between all or a portion of the at least two upstanding elements.

11. The system of claim 9, wherein the sidewall does not have a plurality of apertures.

12. The system of claim 9, wherein the rim includes a plurality of apertures.

13. The system of claim 9, wherein the liner engages contours of the interior and the rim of the tray.

14. The system of claim 9, wherein the liner is disposable and is substantially impermeable to fluids.

15. The system of claim 9, wherein the lid comprises a non-return valve to seal the lid with the tray.

16. A system for storage of an endoscope, the system comprising a polymeric tray comprising an interior for storage of the endoscope, the interior having an upstanding element having a top surface; a plurality of apertures disposed on at least a portion of the top surface of the upstanding element; a sidewall and a rim disposed about the interior of the polymeric tray; a lid comprising no apertures and a non-return valve to seal the lid with the polymeric tray; the lid configured to engage the rim; and a liner configured to engage the rim of the polymeric tray.

17. The system of claim 16, wherein the interior comprises at least two upstanding elements spaced apart from each other to provide support for a flexible medical endoscope coiled between all or a portion of the at least two upstanding elements.

18. The system of claim 16, wherein the sidewall does not have a plurality of apertures.

19. The system of claim 16, wherein the rim includes a plurality of apertures.

* * * * *